US011255815B2

(12) United States Patent
Galen et al.

(10) Patent No.: US 11,255,815 B2
(45) Date of Patent: Feb. 22, 2022

(54) USING ELECTROPHORESIS FOR DISEASE DETECTION BASED ON CONTROLLED MOLECULAR CHARGE

(71) Applicant: HEMEX HEALTH, INC., Portland, OR (US)

(72) Inventors: Peter Galen, Portland, OR (US); Ariane Elizabeth Erickson, Portland, OR (US); David Richard Bell, Issaquah, WA (US); Matthew Christian Lind, Portland, OR (US); Tyler Witte, Portland, OR (US); Umut Atakan Gurkan, Shaker Heights, OH (US)

(73) Assignee: Hemex Health, Inc., Portland, OR (US)

( * ) Notice: Subject to any disclaimer, the term of this patent is extended or adjusted under 35 U.S.C. 154(b) by 0 days.

(21) Appl. No.: 17/232,130

(22) Filed: Apr. 15, 2021

(65) Prior Publication Data
US 2021/0325341 A1    Oct. 21, 2021

Related U.S. Application Data

(60) Provisional application No. 63/010,570, filed on Apr. 15, 2020.

(51) Int. Cl.
*G01N 27/447* (2006.01)
(52) U.S. Cl.
CPC .............................. *G01N 27/44726* (2013.01)
(58) Field of Classification Search
None
See application file for complete search history.

(56) References Cited

U.S. PATENT DOCUMENTS

| 5,863,401 A | 1/1999 | Chen |
| 2006/0194306 A1 | 8/2006 | Herr et al. |

FOREIGN PATENT DOCUMENTS

| DE | 3811083 A1 | 10/1988 |
| EP | 0401821 A1 | 12/1990 |

(Continued)

OTHER PUBLICATIONS

International Search Report and Written Opinion, dated Jul. 29, 2021, in PCT Patent Application PCT/US21/27566, International filing date Apr. 15, 2021.

(Continued)

*Primary Examiner* — J. Christopher Ball
(74) *Attorney, Agent, or Firm* — Lane Powell PC

(57) ABSTRACT

Electrophoresis is used to identify presence of a target compound in a patient sample based on a charge state of the compound and a label. The charge state of the compound correlates to a total net charge of a binder conjugated to the compound. The bound complex or "bound complex" with the label is then applied to the electrophoresis substrate. An electric potential is applied to the substrate for a time period and causes the labeled bound complex to migrate toward the electrode with opposite charge of the labeled bound complex at a migration velocity to form a migration pattern over the time period. At some time during or at the end of the time period, the labeled bound complex produces a bound complex band as a result of its migration across the substrate. The presence of the compound is identified based on the labeled bound complex band and one or both of the migration pattern and the migration velocity.

27 Claims, 14 Drawing Sheets

(56) References Cited

FOREIGN PATENT DOCUMENTS

| EP | 1785724 A1 | 5/2007 | |
|---|---|---|---|
| WO | 1995020161 A1 | 7/1995 | |
| WO | 2008097803 A1 | 8/2008 | |
| WO | 2016019142 A1 | 2/2016 | |
| WO | WO-2016019142 A1 * | 2/2016 | ............. G01N 33/49 |

OTHER PUBLICATIONS

Chu Benjamin et al: Movement of fluorescence pattern after photobleaching: An accelerated procedure for DNA electrophoretic mobility analysis11 , Electrophoresis, vol. 13, No. 1, Jan. 1, 1992 (Jan. 1, 1992), pp. 536-541, XP055824874, ISSN: 0173-0835, DOI: 10.1002/elps.11501301110, abstract.

"Yang F B et al: 11 A low-cost light-emitting diode induced fluorescence detector for capillary electrophoresis based on an orthogonal optical arrangement 11, Talanta, Elsevier, Amsterdam, NL, vol. 78, No. 3, May 15, 2009 (May 15, 2009), pp. 1155-1158, XP026005630, ISSN: 0039-9140, DOI: 10.1016/J.TALANTA.2009. 01.033 [retrieved on Jan. 24, 2009] the whole document.".

Katzmeier Florian et al: 11 A low-cost fluorescence reader for in vitro transcription and nucleic acid detection with Cas13a 11, PLOS ONE, vol. 14, No. 12, Dec. 18, 2019 (Dec. 18, 2019), p. e0220091, XP055824500, DOI: 10.1371/journal.pone.0220091 Retrieved from the Internet: URL:https://storage.googleapis.com/plos-co rpus-prod/ 10.1371/journal.pone.0220091/1/p one.0220091.pdf?X-Goog-Algorithm=GOOG4-RSA-SHA256&X-Goog-Credential=wombat-sa@plos-prod.iam.gserviceaccount.com/20210714/.

* cited by examiner

USING ELECTROPHORESIS FOR DISEASE DETECTION BASED ON CONTROLLED MOLECULAR CHARGE

CROSS-REFERENCE TO RELATED APPLICATIONS

This application claims priority and benefit from the U.S. Provisional Patent Application 63/010,570, filed Apr. 15, 2020 and titled, "INFECTIOUS DISEASE DETECTION & DIAGNOSTICS," which are incorporated herein by reference in their entirety for all purposes.

BACKGROUND

Electrophoresis and immunoassays are both powerful tools used to test for many disease conditions. These include infectious disease, chronic disease, measurement of metabolic condition and many more. The tests to diagnose and manage these diseases are generally expensive, slow, and complex and require a central laboratory, or if used in a remote location, may not offer the sensitivity and performance required for an accurate determination. Disease diagnostics are critical to global health in all countries—developing and developed—to prevent community spread of infectious disease and undiagnosed chronic disease and to avoid unnecessary morbidities and mortalities. Oftentimes, disease diagnostics need a requisite concentration of disease agent or marker—such as a protein associated with, produced by, or produced in response to a virus or a sugar complex on a biomarker—in a patient's sample before the diagnostic tool can detect the disease. Unfortunately, infected patients, for example, are required to wait a period of time after a suspected or confirmed exposure to the disease to allow for the diagnostic tool to give a result with clinically acceptable sensitivity and specificity. Symptomatic patients may experience delays in effective treatments during this wait period because medical personnel are unable to confirm a diagnosis with enough statistical certainty until the wait period expires and the disease condition is confirmed by the diagnostic test. People may be unaware of their infection during this wait period, which results in unintentional community spread of the disease including to other people who may be more medically fragile than the originally infected person. This wait period for conventional infectious disease diagnostics can last several days to a week or sometimes longer and is dependent upon the concentration of the disease biomarker in the patient sample that can be detectable with the available diagnostic tools.

Patients suffering from chronic disease likewise suffer from insufficient diagnostic testing that is expensive and does not have the desired sensitivity and specificity. Oftentimes, these chronic patients suffer high rates of morbidities and mortalities because they go undiagnosed due to lack of affordable and available testing.

Conventional disease diagnostics with the highest sensitivity and specificity require laboratories to process the patient samples, which are expensive resources not widely available in underserved regions. These laboratories can also become overwhelmed during periods of higher rates of infectious disease in a community in developing and developed countries alike because their disease testing techniques often require substantial time and expensive equipment to conduct. For example, patients presumed to be infected with the novel coronavirus of 2020—severe acute respiratory syndrome coronavirus 2 (SARS-CoV-2)—that causes coronavirus disease (COVID-19) typically give a nasal-pharyngeal or oropharyngeal sample that is tested in a laboratory using a highly sensitive reverse transcriptase polymerase chain reaction (RT-PCR) technique in which the ribonucleic acids (RNA) or other nucleic acid of the virus are isolated for detection and, in some cases, amplified to confirm an infection.

The RT-PCR diagnostics are powerful tools; however, they also require sophisticated laboratory equipment to isolate and amplify the RNA and skilled laboratory technicians to perform analysis of the results. Further, the laboratory equipment that isolates and amplifies the nucleic acid segments of the target virus is expensive. Even in developed countries like the United States, community need for such equipment is often driven based on typical infectious disease testing needs, rather than pandemic or epidemic conditions. Scaling infectious disease diagnostics laboratories along with skilled personnel and sophisticated equipment to meet greater than normal testing needs is an expensive and lengthy process that often trails the need so greatly to make its return on the investment in resources poor or nearly non-existent. Developed countries are slow to respond to this scaling need for many reasons including a lack of resources and infrastructure. Sadly, developing countries cannot respond to this scaling need at all because the infrastructure never existed or due to a severe lack of resources. A similar effect happens with chronic disease especially in underserved areas. Often the tests are too expensive or require infrastructure that does not support transporting samples to a remote central laboratory or effectively communicating results.

In general, global health is increasingly in need of highly sensitive-highly specific point-of-care (POC) diagnostics for patients to deliver faster, more accurate results close to the patient. One type of POC diagnostic device is a rapid diagnostic test (RDT) that is designed for low-cost, mass scale deployment to clinical and non-clinical settings. Faster, more accurate results allow sick patients to receive treatment—sometimes life-saving treatment—sooner, allows community leaders to set informed healthcare and economic policy, and gives healthcare personnel much needed diagnostic infrastructure support to find and treat ill patients. These POC diagnostics improve community health and safety and avoid overwhelming critical care treatment facilities so that the most severely infected or ill patients can easily access treatment. Early diagnosis helps reduce the risk of untreated infection or underlying chronic condition becoming severe and of unnecessary community spread of myriad diseases ranging from infections like malaria, measles, and SARS-CoV-2, to chronic diseases like cancer, coronary artery disease, and thyroid disease. Also, POC diagnostics need to be easy to operate and do not require highly skilled technicians to determine a diagnostic result. Still further, POC diagnostics tend to be much less expensive than laboratory tests, which makes their deployment in developing countries and on mass scales in developed countries realistic and effective.

Currently, available POC diagnostics for many diseases—including COVID-19—often suffer from a low sensitivity and specificity, which, for example, makes it difficult to discriminate patients with a confirmed infection from patients with a confirmed healthy or non-infectious sample. Many POC diagnostics detect antigens, antibodies, or biomarkers associated with a health condition—such as SARS-CoV-2 virus nucleocapsid protein for COVID-19 or histidine-rich protein-2 (HRP2) for malaria—using lateral flow assays that require relatively high concentrations of the compound to be present in the patient sample. These tests can give uncertain or inconclusive results (e.g. a band that is very faint or is not detectable by available equipment or personnel, which make a visual determination of the results difficult or impossible), or simply are performed incorrectly due to lack of trained personnel or errors. They also rarely provide a quantitative result—the actual concentration of the biomarker of concern, which can be critical to clinical decision-making.

These drawbacks limit the use and effectiveness of POC diagnostics for many diseases, especially those where the concentrations of the compound being tested are low—making the process of obtaining accurate results unreliable and become positive too late in the disease course to best treat patients and limit community impact of the disease. The limitations of the POC diagnostics for diseases like COVID-19 can lead to unintentional disease spread, waste of valuable healthcare resources, and unnecessary isolation of healthy patients presumed infected due to a false-positive test result, among many other immediate and downstream health, safety, and economic consequences.

Therefore, the healthcare industry needs improved disease diagnostics that are highly-sensitive, highly-specific, faster, affordable and easy to use and that can be deployed on a mass scale all over the world.

SUMMARY

Disclosed methods and systems identify the presence of a compound in a patient sample using electrophoresis. The presence of the compound is based on a charge and mass profile of a binder that binds to a target compound to create a bound complex or bound complex with a controlled compound charge state and mass. The controlled compound charge and mass state is the total net charge of the binder and compound. The binder has a consistent binder charge and mass profile that, when bound with the known charge and mass of the target compound, creates the concentration of a bound complex having a compound charge and mass state with the controlled total net charge and mass. The bound complex and remaining unbound binder are then applied to a substrate. In some examples, the substrate is an electrophoresis substrate to which an electric potential is applied for a time period. Bound complex and unbound binder are attracted to the electrode of the opposite charge and migrate across the substrate at a constant or varying migration velocity over the time period when the electric potential is applied. The different migration velocities of the bound complex and unbound binder at their migration velocities creates a migration pattern on the substrate over the time period. The migration of the bound complex and unbound binder over time at the migration velocity ultimately results in bound complex and unbound binder band(s) during or at the end of the time period. The migration pattern dynamically changes throughout the time period as components on the substrate—including the bound binder-target complex—migrate in response to the applied electric potential. Presence of the compound is identified based on the band(s) and one or both of the migration pattern and the migration velocity. The migration pattern on which the presence of the compound is determined can be any one or more image capture(s) or continuous imaging segment(s) during or at the end of the time period.

Additionally, the binder or the target compound has a label that is visible or optically detectable. Without a label or staining binder, target compound or bound complex are oftentimes not optically detectable. Use of a label with the binder or target compound enhances the ability to detect them without the need for staining and washing normally used in electrophoresis immunoassays. In addition, a fluorescently labeled bound complex is detectable at much smaller concentrations than with standard staining. The label is added to either the binder or the target compound before the binder conjugates to the target compound. The labeling of binder or compound creates a labeled bound binder-target complex. Specifically, the labeled bound complex having a controlled charge and mass profile allows for optically detectable bands to form in the migration pattern and, in some examples, during the active assay run.

BRIEF DESCRIPTION OF THE DRAWINGS

Non-limiting and non-exhaustive embodiments of the invention are described with reference to the following drawings. In the drawings, like reference numerals refer to like parts throughout the various figures, unless otherwise specified, wherein.

DETAILED DESCRIPTION

Figure 1:
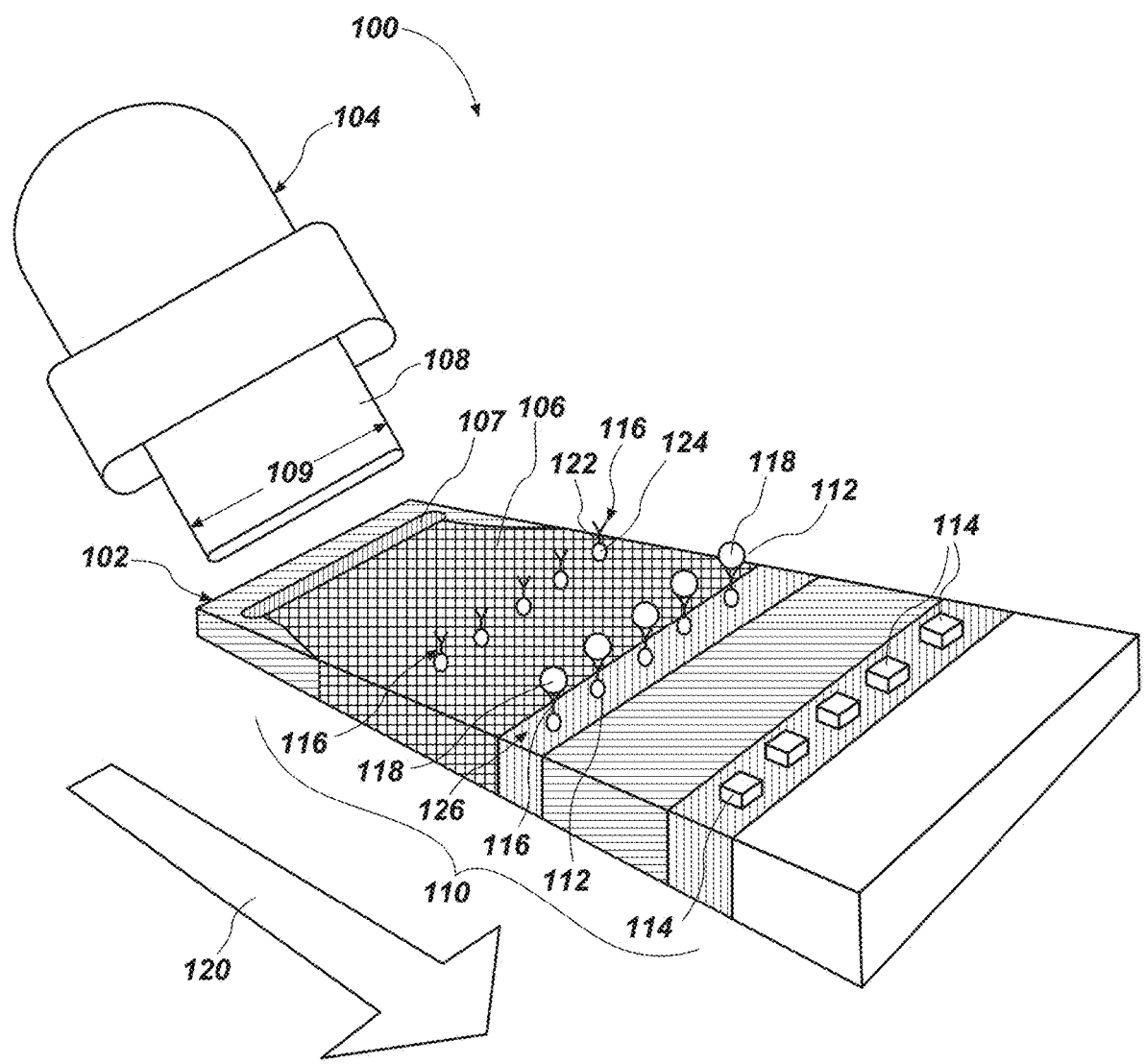
FIG. 1 shows an example substrate with a prepared patient sample applied to it, according to aspects of the disclosure.

The subject matter of embodiments disclosed herein is described with specificity to meet statutory requirements and to convey the scope of the subject matter to those skilled in the art, but this description does not limit the scope of the claims. The disclosed subject matter may be embodied in other ways, may include different elements or steps in the same or a different order, and may be used in conjunction with other existing or future technologies.

The disclosed diagnostic methods and systems are able to provide highly-sensitive, highly-specific test results using a patient sample with a low concentration of target compound.

The test focus can be an infectious or chronic disease, metabolic state, or a pre-disease condition. A target compound is a compound or biomarker of interest for which a patient sample is being tested. The target compound in immunoassays, for example, is often an indicator or biomarker—antigen, antibody, byproduct, or otherwise—of an infection or disease state or pre-condition in a patient. The target compound is the measurable component of the patient sample that can determine whether or not the patient is infected with the disease, has a pre-disease condition, or is experiencing a metabolic state of interest (e.g. pregnancy or ingestion of a compounds like a performance enhancing substance). The patient sample can be any suitable tissue or fluid sample from the patient. For example, most commonly in POC diagnostics, the patient sample is blood, nasalpharyngeal or oropharyngeal fluids, urine, saliva, mucus, tissue cells, and the like. A patient can be human or animal. The patient sample can also be a plant sample or other non-biologic sample as well.

The disclosed methods and systems can take advantage of existing POC electrophoresis systems, such as the Gazelle® platform commercially available from Hemex Health®, Inc. or other POC electrophoresis devices. Many conventional fluorescent immunoassays do not consider charge or mass of the binder, the compound, or the bound complex as part of the analysis because charge is not relevant to the migration of those compounds on the assay. This is especially true when optically detectable labels are included. For example, a lateral flow assay is based on flow of a patient sample along a substrate and over one or more control lines to which some target compound or biomarker would bind if it is present in the patient sample. Throughout this disclosure, reference to the target compound includes any compound, molecule, biomarker, or other indicator of disease, predisease condition, or metabolic state. Lateral flow assays do not rely on an applied electric potential to generate the migration of any compounds so whether a molecule has a total net charge or is in a particular charge state is not relevant to the compound's ability to migrate across the substrate and bind with test lines.

In diseases such as COVID-19 and hepatitis C, the level of antigen available for detection of disease the pathogen is very low, which produces low sensitivity and specificity in standard lateral flow tests. For example, the required antigen level for hepatitis C is around 3 femtomols (fmol) per liter. This concentration of target compound in the patient sample conjugates with the binder to form a bound binder-target complex having a total net charge and a mass. The binder is a molecule that attaches to the target compound to create the bound complex—oftentimes, the binder, rather than the target compound is the detectable component of the sample. For example, if the target compound is an antigen, such as a protein produced by or produced in response to a virus, the binder is an antibody conjugated to the antigen or an epitope of the virus protein in this example.

A label is attached to either the binder or the target compound to produce a labeled bound complex—labeling of the binder or compound can occur before or after the binder and compound are conjugated. This prepared patient sample includes a labeled bound binder-target complex. Patient samples without compound—for example, healthy patient samples or patients for whom the absence of the target compound or biomarker indicates a disease state—results in a prepared patient sample that includes unbound binder with its label, which can be either a substance visible in white light like a dye or a fluorescent label or "fluor." No bound complex is present in the healthy patient sample, in some examples in which positive identification of the target compound indicates disease. In other examples, absence of the target compound indicates the disease state itself, such as in some hemoglobin disorders. The presence of the label on the bound complex allows for small concentrations of bound complex to be detected because the label is detected in the captured image rather than the bound complex itself. In some examples, the label is a substance that is visible in white light. That substance becomes attached to the labeled bound complex and is then visible on the captured image(s). The label increases the ability of the optical imager to detect presence of the label in small concentrations of bound binder-target complex. Even if the target compound band is not visible, the label may be visible and then becomes the molecule indicating presence of the target compound.

The label can also be a fluorescent label or "fluor" that responds to an excitation energy with a fluorescence emission. A fluor is a molecule that responds to an energy source such as light from a light-emitting diode (LED) or energy from a laser, with a responsive energy emission of its own. Many materials naturally have a certain fluorescence in response to an excitation energy, such as light at a particular wavelength. Some materials can be excited to fluoresce with a responsive energy emission of a particular behavior that is well defined enough to separate them from the background materials. The energy emission of the fluor is a different wavelength or range or wavelengths from the light or energy emitted from the excitation source. Often, the fluor has a time delay, in the nanosecond range in some examples, in which it then emits its fluorescence even after the energy source of excitation is turned off or removed. Certain compounds such as europium can persist for 600 microseconds or longer after excitation begins or is removed. The fluorescence emission from the fluor appears in the captured images. Without tight control over the charge state and the mass of the bound complex to which the label is attached, the images of the labeled bound complex would migrate at multiple velocities, which causes a smear because of the different migration velocities corresponding to the different molecules or would produce results that could not be used to discriminate whether the target compound was present.

In an example, the fluor is attached to the binder. The binder conjugates to the target compound upon mixing with the patient sample. Unbound binder remains in the sample as well. Both the bound complex and the unbound binder are fluorescently labeled in this example. The bound complex is separated into its charge states. A selected charge state of the labeled compound is important to allow electrophoresis to occur without confusion between bands—there is clear band separation because molecules of like charge and mass migrate together—and the fluor allows for small concentrations of the target compound to be discovered and appear as a band in the images captured by the optical imager. Together, the fluors on the charge- and mass-controlled target compounds create clear bands of target compound in small concentrations using electrophoresis.

Further, photobleaching the substrate reduces the natural auto-luminescence of the substrate and further enhances the band detectability. Other components of the system can also be photobleached to reduce or eliminate their auto-luminescence. Photobleaching can occur during manufacturing or right before the test. Typically, the substrate or other system components are photobleached during manufacturing—in the example of the substrate—or prior to the test being run. Photobleaching reduces the auto-luminescence of the substrate, which means that the fluors on the bound complex appear brighter or to have higher intensity in the captured image(s). Photobleaching involves illuminating the substrate for a period of time with intense light, which can be a single wavelength or multiple wavelengths like high intensity ultraviolet (UV) light or broadband white light, to reduce the autofluorescence of the substrate. By reducing the auto-luminescence, the space between bands is darker on the substrate, which allows detection of a fainter band because its intensity is more detectable against the darker background. Reducing surrounding natural auto-luminescence of the substrate increases the differential of the band intensity of the bound complex to its substrate and to the intensity of other bands. Further, controlling the wavelength of the light from the energy source used to excite the fluors helps control the auto-luminescence of the substrate, for example. Many substrate materials, such as cellulose acetate and nitrocellulose have increased autofluorescence when illuminated with ultraviolet, blue, or green light and responsively emit blue or green light. Working with excitation light in the red wavelength range with emissions in the red or infra-red range minimizes much of this autofluorescence. Choosing a fluor with these characteristics reduces the impact of autofluorescence of the substrate and other components.

Conventional electrophoresis does not use fluorescence for several reasons including the target compounds typically require much high concentrations for band separation and ultimately optical detection and the bands produced are not clear or readable due to the lack of control of the molecular charge and mass and because of auto-luminescence of surrounding materials like the substrate. Conventional fluorescent immunoassays do not consider molecular charge because the flow or molecule separation occurs without application of an electric potential. The disclosed methods and systems that include a labeled bound complex overcome these challenges of the conventional methods to improve sensitivity and specificity and to lower the volume of detectable compound concentration required for the tests.

In typical electrophoresis, a fluor would cause a bleeding of results from molecules of varying charge states or what appears as a smear on an imaged substrate. This undesirable result previously prevented electrophoresis from being used with fluorescently or other labeled binders or compounds. In capillary electrophoresis, for example, the compound detector is positioned at a fixed location along the capillary tube and measures compound as it moves through the fluid or gel past the detector. Capillary electrophoresis does not rely on an optically detectable migration pattern on a substrate over time, as the disclosed methods and systems teach. For those healthy patient samples, the fluorescently labeled unbound binder would fluoresce alone. If the charge state and mass of the unbound binder is not controlled, the unbound binder would also produce a smear on the image due to it being in multiple charge and mass states.

In this disclosure, the compound charge state of the bound complex is the total net charge of the bound binder-target complex, —including the binder charge and the compound charge—which is uniform throughout the entire prepared patient sample to give the bound complex of the patient sample a uniform or "controlled" total net charge. If the conjugation of the binder and the target compound is not controlled at a fixed ratio, the charge is not uniform but instead has various discrete values that cannot be discriminated using electrophoresis. The prepared patient sample is applied to an electrophoresis substrate, which is the medium on which the patient sample is placed for testing. In electrophoresis, the patient sample is applied to the test medium, which is often a paper or gel. Then, an electric potential is applied to the substrate across two electrodes positioned on either side of the applied patient sample. In standard POC electrophoresis techniques, the bound complex and all electrically charged components in the patient sample migrate across the substrate in response to the applied electric potential. All of the bound complex molecules generally migrate together, evenly or within a "band" toward the electrode of opposite charge because the total net charge and mass of the bound complex is generally uniform or controlled and thus drawn to the oppositely charged electrode with the same electric field force.

The band is a collection of the component molecules that migrate with the same total net charge and the same mass. Small variations in mass or charge can be tolerated to still create a controlled band of molecules with the target compound. For purposes of this disclosure, "same" is intended to include small variations as well. This bound complex band is the collection of molecules of like charge and mass that have a common migration velocity. The band is the visual representation of the migrating molecules of like characteristics. The applied electric potential causes the molecules of like charge and mass to migrate or physically move a consistent distance at a consistent or uniform velocity. Because the small variations in charge and mass and other ambient environmental factors, some of the molecules with like charge and mass may have a migration velocity within a small range—the migration velocity of the molecules may slight vary. Here, reference to the "same" migration velocity also includes this small variation and still produces the disclosed controlled band that is optically detectable. The molecules of like charge and mass also migrate off the substrate or stop migrating if the electric potential is removed at about the same time and about the same distance—the migrating or stationary band of like characteristics is optically detectable on the substrate. In some examples, all of the migrating component bands are detectable by an optical imager. Some component bands may be difficult to optically detect or may not be optically detectable because their intensity is too low for detection. Labeling the bound complexes increases the intensity of the faint and undetectable bands so they become detectable by the optical imager. Other compounds produce a band with a higher opacity when labeled, which makes them easier to optically detect. This is especially true if the target compounds are all labeled with a fluorescent molecule.

The binder can be labeled or has intrinsic properties that allow it to be imaged. For example, the binder could be colorimetric, fluorescent, luminescent, or the like that is able to be optically detected when present in a band. These binders ensure consistency of charge and mass between each labeled binder to enable direct optical detection of the bands of concentrated bound complex and unbound binder during migration.

Examples of the disclosed disease diagnostic methods and systems are immunoassays that are performed on paper or gel electrophoresis substrates, such as cellulose acetate paper or agarose gel. In response to the applied electric potential, components of the patient sample migrate at respective migration velocities across the substrate toward the electrode of opposite charge based on the respective total net charge or charge state and corresponding masses of the respective components. This migration of components over a time period produces a migration pattern, which is a physical movement of components across the substrate in response to the applied electric potential. The optical imager captures image(s) during and at the end of the time period that reflects the final migration pattern of each of the components in the patient sample. The time period is the period of time in which components applied to the substrate migrate across the substrate. Specifically, the time period starts when the electric potential is applied and ends when it is removed. Without an electric potential, the components do not migrate in a clinically significant manner although there may be some nominal movement.

Alternatively or additionally, the optical imager can capture image(s) during the active assay—when the electric potential is actively applied to the substrate and the active migration occurs—to gain more detailed data on the migration of components throughout the time period. For example, dynamic image capture during the active assay produces data about how a charged molecule behaves throughout the time period rather than merely at the end, which can generate trends in molecular behavior in response to the applied electric potential over the time period and in migration velocity which may help determine or validate existing test results. Migration velocity is the velocity at which a component migrates or physically moves across the substrate in response to the applied electric potential and may be constant or variable in response to the applied electric potential. The migration pattern can include the physical location of the resulting bands of components that migrated across the substrate along with the thickness of the bands, and separation between bands. The migration velocities can be absolute or relative to a control or marker with fixed chemical concentration that co-migrates with the sample.

Further, the migration pattern also can include the dynamic movement of the components as they migrate across the substrate over the time period. For example, the migration velocity of a component can be tracked over the time period. The migration velocity of one component can be compared to the migration velocity of another component or a known standard or reference substance. The migration velocity for any migrating component can be variable or consistent throughout the time period. The change in migration velocity might also be considered along with trends in the migration velocity, thickness of the band, movement of the bands with respect to each other, behavior of the band when no target compound is present, and the like can also be tracked and trends can be extrapolated. Adding dynamic analysis of the migration pattern, including all aspects of component migration characteristics, helps distinguish molecules from each other based on multiple aspects of their molecular characteristic(s) or behavior(s).

Mass of the bond compound is another molecular characteristic that can affect its migration pattern and characteristics, such as migration velocity. Varying the mass of the binder controls the total net mass of the bound binder-target complex. Heavier bound complex moves slower than lighter bound complex in response to an applied electric potential. If a heavier binder is desired for its characteristics, such as its fluorescence response, it moves slower when all other aspects are kept constant. When the binder is conjugated to the target compound, the mass and charge of the bound complex determine migration velocity. The bound complex always has higher mass than the unbound binder. If the charge increases when then binder conjugates with the target compound, the bound complex moves faster; otherwise, it moves slower than the unbound binder. For example, the binder can be chosen to have much lower charge than the target compound that is being detected. When conjugated, this can result in a larger charge differential between the unbound binder and the bound complex, which means the bound complex has a much higher charge than the binder alone. This causes an increase in the differential of migration velocity of the bound complex to the unbound binder. Since the bound complex has greater mass than the binder, it moves slower if the charge is identical or within a small difference to the binder charge. The combined charge is chosen to either slow down the bound complex or speed it up. The change in charge does not negate the increased mass or a new band does not separate. Therefore, the binder charge is carefully selected to create a separate band but not negate the change in mass that inherently occurs with the bound complex molecule.

The disclosed methods and systems use an optical imager to capture relative comparisons of component migrations, either in a single instance (e.g., the end of the migration time period) or throughout the active assay, to determine presence of a target compound in a patient sample. This disclosure discusses determining presence of a target compound in a patient sample in several examples although it can equally apply to determining multiple target compounds in the patient sample using the same or different respective binders. In an example method or system with multiple target compounds, multiple unique binders are tailored for each of the respective target compounds. In another example with multiple target compounds, the same labeled binder conjugates with the target compound to produce a bound complex for each of the target compounds—each of those bound complexes have a different mass and charge because the respective target compounds have different mass and charge.

The binder charge, mass, or combination of the charge and mass can be chosen to change the migration pattern to differentiate a target compound from other compounds in a patient sample, including other target compounds in the case of a "multiplexed" test that is determining whether the patient sample contains more than one target compound. Additionally, binder fluorescence can be selected so that the fluors either excite at different wavelengths, emit at different wavelengths, or both in order to multiplex tests for multiple target compounds.

Presence of the target compound is a detectable amount of the target compound in the patient sample. Some samples from healthy patients have no target compound and would therefore produce only a band indicating the presence of the unbound binder without an indicator that the binder conjugated to the target compound. Further, the optical imager can also optionally capture continuous imaging segment(s), in some examples, during the active assay. The active assay migration pattern is imaged throughout the time period to evaluate the characteristic of the migrating component bands across the substrate, not at a single specific location. This differs from other electrophoresis methods that rely on a single detection point to measure migration of a component, such as capillary electrophoresis through a fluid or gel matrix. It also differs in that the optical imager captures image(s) or continuous imaging segment(s) during the active assay in addition to capturing the migration image at the end of the assay when the time period is expired. The imaging can use one or multiple wavelengths of illumination or fluorescence. For fluorescence, the bound complex, binder, or the target compound may be labeled with a fluorescent reporter, such as the fluors described herein.

As discussed above, adding a label to the bound complex helps to detect the bound complex or the label indicating the bound complex is present in the captured images. In an example, the label is a dye added to the bound complex prepared patient sample. The dye is visible in white light. When the optical imager captures images either at the end of the electrophoresis run or actively during the run, the labeled bound complex is easier to detect on the images with the label than it would be without the label. This permits smaller concentrations of the bound complex to appear on the images as a band because the labeled bound complex appears before the unlabeled bound complex appears, assuming the unlabeled bound complex is visible at any concentration. However, because most unlabeled bound complexes are not visible at any concentration, a label is required to detect the migration of the bound complex band. In the examples in which the optical detector captures image(s) during the active electrophoresis run, the labeled bound complex can appear mid-way through the time period of the run to be compared to its later band migration pattern or other bands that appear over time to identify or validate it is the labeled bound binder-target complex.

In another example, a fluor is attached to the binder or the compound before it becomes a bound binder-target complex. The result is a fluorescently labeled bound binder-target complex, which responds to an excitation energy source, such as a light source. The excitation energy source directs light toward the substrate throughout or during portions of the active electrophoresis run to cause the fluors to respond with its fluorescence emission. The fluorescence emission appears on the captured image(s) generally at lower concentrations of bound complex than would occur with a non-fluorescent optical label. This happens because of this responsive fluorescence emission. Because the fluorescence emission is optically detectable, analyzing the image(s) for presence of the fluor during the active assay allows for the detection of the presence of smaller concentrations of the bound complex throughout the run.

Of course, the image(s) of the substrate at the end of the time period can be used in addition to or alternatively to the images of the active assay, as needed.

Capturing image(s) during an active immunoassay allows for analysis of more aspects of a migration pattern, such as migration velocity of one or more components. Each migrating component in a patient sample has a respective velocity at which is migrates across the substrate in response to the applied electric potential. The migration velocities have a high correlation to the strength of the total net charge and the mass of the components—i.e. its attraction to the oppositely charged electrode. Components with charges farther away from neutral or "0" migrate at a higher velocity than components with charges closer to neutral or "0." For example, a bound complex with a high charge state has the fastest migration velocity, which helps to differentiate it from other slower migrating components—such as unbound binder—for a relative comparison. The ability to evaluate the migration velocity as part of the migration pattern analysis helps to further differentiate a bound target compound from an unbound binder or other patient sample components. Conventional immunoassays only evaluate the image(s) after the immunoassay test run is complete, not during the active assay. Analyzing the migration pattern in the disclosed systems and methods during the active assay helps increase the sensitivity and specificity of its results.

Conventional immunoassay binders may vary in the number of binding sites to which they conjugate on the target compound. For example, simply mixing binder with compound would produce a bound complex having a variety of "charge states" and mass due to variation in the number of binders that conjugate to the number of molecules of the target compound. Most compounds have a specific number of binding sites to which binders may conjugate to create distinct groups of bound complex of like charge and mass. The binder can be selected to substantially increase or decrease the total net charge of the bound complex—the total net charge is directly related to the migration velocity of the component. One binder may add to the total net charge of the compound at a first level while another binder adds to the total net charge of the compound at a second level. The second level could be substantially great than the first level, which drives a faster migration velocity due to its stronger response to the applied electric potential.

This variable number of binders bound to the binding sites of the compound produces a variable total net charge of bound complex—each binder has a binder charge profile that changes the total net charge and mass of the bound complex depending on the number of binding sites to which the binder conjugates. The binder charge profile is the net charge of the binder on its own. For example, if a binder has mass 5 and charge +2 and can bind with up to three compounds—the target compound having mass 7 and charge −2—the resultant bound complexes are: (1) mass 12—charge 0, (2) mass 19—charge −2, and (3) mass 26—charge −4. The first bound complex does not migrate since it has a charge of 0. The second and third bound complex would move in the opposite direction as the binder since their charges are negative. There would be three bands in this case for the bound complex. Label amplify this phenomenon. Many binders can bind to 1-4 labels. If the label, which has negligible mass, has a charge of +1 we now have 12 bands of bound complex for this example binder-target compound complex. These bands are often close together creating the appearance of a smear since the bands cannot be individually viewed.

By targeting only a bound complex with a specific total net charge and mass—compounds with binder conjugated to a fixed number of binding sites on the target compound and with a fixed number of labels—the bound complex can migrate across the substrate at a consistent migration velocity or within a desirable range of migration velocities. Without such control over the total net charge and mass of the bound binder-target complex, the bound complex of varying total net charge and mass migrates at different migration velocities across the substrate, which creates a smear on the substrate rather than clear bands, which, at a minimum reduces the sensitivity of the assay. Smears make obtaining diagnostic results difficult or impossible.

Further, after the patient sample has a bound binder-target complex, the bound complex can be separated into its respective charge states that correlate to the charge intensity or total net charge of the charge of the bound binder-target complex. For example, a fluor with a neutral charge is selected or a fluor with a specific charge state is selected. If a fluor with a neutral charge state is selected, then the labeled binder has the same charge state irrespective of the number of fluors attached to each binder molecule. In this example, the labeled binder would have a slightly heavier mass with the conjugation of the label(s) although that additional mass is negligible because the mass of a label is small compared to the overall mass of the binder molecule. Alternatively, the fluor is selected with a specific charge state, which is discussed in more detail below in reference to FIG. 4. More complex fluors with multiple charge states need to be filtered before they are incubated with the patient sample. The filtering of the fluorescently labeled binder results in a concentration of labeled binder of the same charge state and mass, which is then incubated with the patient sample. For example, fluors could have a charge of −3, −6, and −9—three distinct charge states—that are then fractionated before or after conjugating with the binder to a single charge state for the fluors or the fluorescently labeled binder, respectively. Even further, a binder can be chosen that has a single binding site so that its charge state can only change to an expected bound charge state when the fluor conjugates to the binder—only one binding site is available to which the fluor can conjugate.

Some examples of the disclosed methods and system also include a fluorescent label or optical reporter that labels the binder that conjugates with the target compound. An optical reporter is optically detectable at one or more wavelengths but does not necessarily include fluorescence. A fluorescent label is a molecule or compound that "fluoresces" or glows at an emission wavelength(s) in response to excitation from an energy source, such as a laser or a light-emitting diode (LED) at a different wavelength than the emission wavelength. The fluorescent emission of the fluorescence label is in response to its excitation. The fluorescence emission of the fluorescence label occurs for a period of time, that can continue for a time after the excitation source is turned off. For example, europium is used as a fluorescent label or fluor in the disclosed methods and systems. Europium is typically excited at around 365 nm and has peak emissions around 610 nm. It continues its emission for at least 600 microseconds after the excitation source is turned off. Alternatively, other fluorescent labels can also be used, such as atto 665, Rho14, and alexafluor 488.

Alternatively, the target compound itself is labeled with the fluorescent label or optical reporter. Either way, the resulting bound compound in a prepared patient sample has a label. During or after the migration of the target compound and the other compounds in the patient sample, a fluorescence exciter—such as a laser or LED—is directed toward the substrate to cause the fluorescent label to "fluorescence" or emit its responsive transmission of light or to illuminate the fluor or optical reporter. For fluorescence the labeled bound compound is detected by a fluorescence detector, which can be integrated with the fluorescence exciter in some examples. When florescence of an expected wavelength is detected, the target compound to which the fluorescent label is bound is known to be present.

Combining this optional fluorescence detection technique with the technique to evaluate the migration pattern of a target compound—possibly relative to other migrating components in the patient sample—is a powerful tool to create highly-sensitive, highly specific diagnostics using small concentrations of the target compound. As mentioned above, this concept extends to detecting multiple target compounds as well as detecting one target compound.

Turning now to FIG. 1, an electrophoresis test 100 that includes a substrate 102—in this example the substrate 102 is a cellulose acetate paper strip—and a patient sample applicator 104—in this example the applicator 104 is a stamper. The stamper 104 contains or stores a prepared patient sample 106 that is applied to the substrate 102. The prepared patient sample 106 is applied to the substrate 102 along a compact application line 107. The compact application line 107 places all molecular components in the prepared patient sample within a small physical space to begin the migration process. If all of the charged molecules begin at this controlled application line 107, then their respective migration begins from that line and can progress together until the compounds of differing charge, mass, or both begin to separate during the migration process. If instead, the patient sample is applied to the substrate as a blot onto the substrate or deposited as a droplet onto the substrate, the molecules of like charge and mass migrate at the same migration velocity but begin from different starting positions. The different starting positions of molecules with like charge and like mass produce a thick band or do not appear as a band at all and transform into a smear on the substrate.

The patient sample chamber 108 of the stamper 104 has a width 109 that extends across the much of the width of the substrate 102 to produce the compact application line 107. The patient sample chamber width 109 can be just slight less than the width of the substrate 102 itself to create the application line 107 across most of the width of the substrate 102. Because the application line 107 extends across most of the width of the substrate 102, the band begins to form across the width of the substrate 102 when the molecules start to migrate in response to the applied electric potential. FIG. 1 depicts an ideal test in which molecules of like charge—the labeled binder 116, the bound complex 126, and the marker compound 114—migrate perfectly aligned with each other. In practical environment, a small migration variation can occur between molecules of like charge and like mass due to nominal variations in charge or mass between molecules and the exact placement within the application line 107. While the application line 107 is a practical attempt to apply the patient sample to the substrate in a way that allows all molecules of like charge and like mass to begin to migrate from the same physical location on the substrate, it is not possible for it to be exact but is instead has an inherent thickness, however narrow. The inherent thickness of the migration of molecules of like charge and like mass correlates to the thickness of the resulting band after the electric potential is removed.

In this example, a patient sample chamber 108 of the stamper 104 releases the prepared patient sample 106 onto the cellulose acetate paper strip 102 at the application line 107. This cellulose acetate paper strip 102 shows a migration pattern 110 of a bound complex 112 and a marker compound 114 after an electric potential has been applied to the substrate 102 for a time period. Binder 116 is shown conjugated to the target compound 118 and separating into a bound complex band along the direction of migration 120. The bound complex has binder 122 with a fluorescent label 124 and a consistent or uniform compound charge state. For example, the binder 122 has a pH 8.3 and a charge of approximately −3 and the target compound has a neutral charge. This binder charge profile of −3 could conjugate to the target compound 118 in one to four binding sites—which creates four charge-mass profiles with different charge and mass—that would vary the total net charge of the bound complex 112 between −3 and −12 and correspondingly vary the mass of the bound complex 112 in the same manner. The binder 116 is designed and refined such that only a single (or a fixed) number of conjugations can occur. In an example, the fluor is selected to have a neutral charge that does not alter the charge state of the binder when the fluor conjugates to the binder. Further, because fluors are typically very low in mass, especially compared to binder molecules, adding neutral fluors to a binder does not substantially change the mass of the fluorescently labeled binder compared to the mass of the unlabeled binder. Alternatively, the disclosed methods and systems have a fluor with a specific charge state, that is able to be filtered or that can be fractionated to a single charge state before or after conjugating to the binder, such as by using anion exchange chromatography. Alternatively, a binder is chosen that only has a single binding site so that its charge state can only change to an expected bound charge state when the fluor conjugates to the binder—only one binding site is available to which the fluor can conjugate.

During preparation of the patient sample, for example, the binder 116 conjugates with the target compound 118 in an incubation step that can be a short period of time, such as several minutes, to allow the sample to sit at room temperature to create the bound complex 112 that having a uniform, single charge and mass state. The uniform charge-mass state for the bound complex 112 moves across the substrate 102 with a migration velocity to form the bound complex band 126.

This example prepared patient sample 106 also includes marker compound 114, which is a controlled concentration of a molecule in a different charge-mass state than the charge-mass state of the bound complex 112 found in the prepared patient sample 106. The marker compound is typically a different chemical than the target compound or the binder and has a corresponding marker charge and mass. The differential in the charge and mass of marker compound to the charge and mass of the bound complex produces images with intensities that can be compared based on the known properties of the marker compound. The marker produces a migration pattern distinct from the migration of the bound complex 112 or the unbound binder 116. The marker compound 114 in this example has a higher charge state—or more negative charge than the bound complex 112—that causes it to migrate faster along the substrate 102 than the bound complex 112. The maker compound 114 migrates further along the substrate 102 than the bound complex 112 because it is more negatively charged than the bound complex 112 so it is drawn more rapidly and thus closer to the positive electrode (not shown) by the applied electric potential.

The migrated marker compound 114 produces a marker compound band 128 that is a guide against which the other bands are compared. The marker compound 114 has an expected migration pattern because of its unique mass and charge compared to the target compound 118, the labeled binder 116, or the bound complex 112. In response to the applied electric potential and because its charge-mass state is fixed and differs from the other molecules in the sample, characteristics of the bands produced by other molecules in the sample can be compared to it as a point of reference. The marker compound band 128 appears when the bound complex 112 is present and when it is not present in the prepared patient sample 106, which makes it a "marker" or guide to which relative comparisons of other bands are made, such as the bound complex band 126. Any other band that appears can be measured against the marker compound band 128 and the known characteristics of its migration pattern and migration velocity. The marker compound band provides a normalized reference and can also act as a control to ensure the electrophoresis process is working correctly with the velocity and intensity being within expected parameters.

In a patient sample with no target compound 118, the migration pattern 110 would include the marker compound band 128 alone without a bound complex band 126. The unbound binder 116 that is mixed with the patient sample has its own charge-mass profile, so it migrates when the electric potential is applied to the substrate 102 to create an unbound binder band (not shown in FIG. 1). The unbound binder band has distinct characteristics from the bound complex band in migration pattern—its migration velocity, distance, and band thickness, for example—and a distinct charge-mass profile. The unbound binder migration pattern and migration velocity differs from both the bound complex migration pattern and migration velocity and the marker compound migration pattern and migration velocity. Because the unbound binder has a known charge and migration profile, it is another marker or control band that can be used as a relative comparison to any bound complex band that appears. The binder, labels, fluorescent labels, pH, and other molecular characteristics of each component are chosen to ensure each of these elements creates a unique band distinct from the others.

Figure 2A:
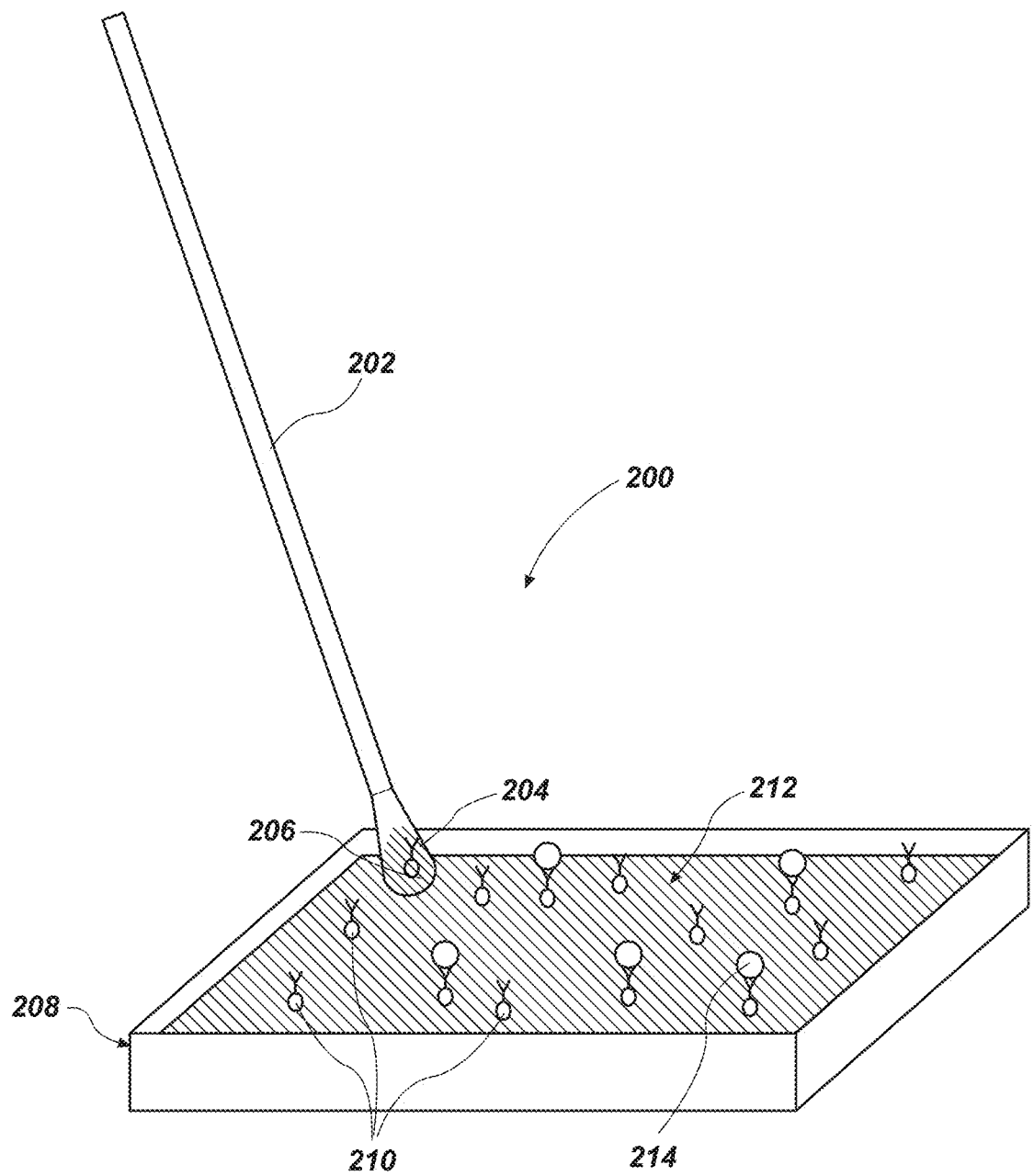
FIGS. 2A and 2B show an example patient sample and patient sample preparation with a target compound or biomarker.
Figure 2B:
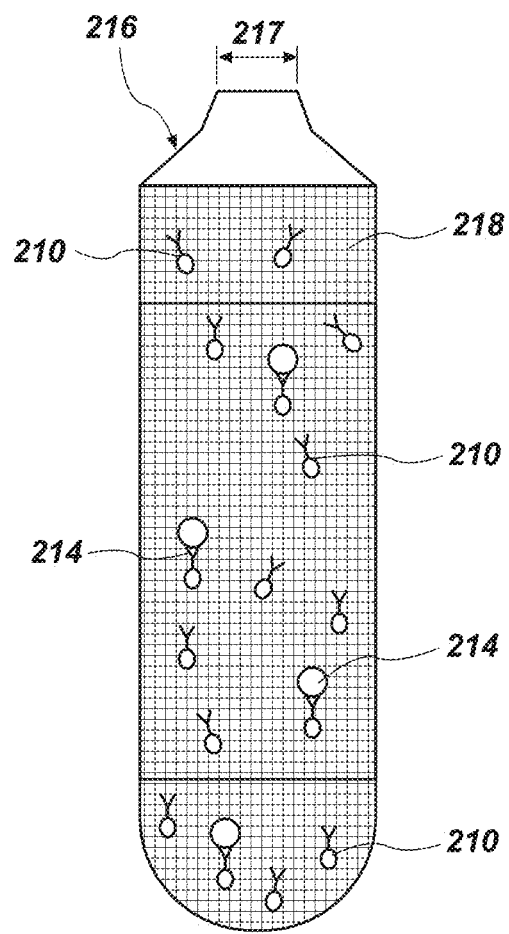

Turning now to FIGS. 2A and 2B, a patient sample preparation 200 has a patient sample collector 202 with a patient sample 204. FIG. 2A shows a patient sample 204 with the target compound 206 on the sample collector 202. The sample collector 202 in this example is a swab stick, but it could be any suitable sample collector and differs based on the type of patient sample being collected for the test. The patient sample 204 is being shown here to be placed in a preparation chamber 208 that has labeled binder 210. In this example, the label could be a dye or a fluorescent label, such as a fluor that emits after being excited at a light emission at an excitation wavelength. Some of the labeled binder 210 conjugates to the target compound 206 while some of the binder remains as unbound binder 210 in the prepared patient sample 212. FIG. 2A shows a simple preparation chamber 208, and any suitable preparation chamber 208 could be used, including those that are integrated into a reader or other diagnostic system equipment or into a cartridge that prepares the sample for insertion into a reader or other portion of a diagnostic system. FIG. 2A shows a prepared patient sample 212 with unbound binder 210 and labeled bound complex 214 that produces a positive result for presence of the disease or biomarker.

FIG. 2B shows a cartridge 216 having a width 217 of its applicator tip that contains the prepared patient sample 212 as it incubates with unbound binder 210 and labeled bound complex 214. The width 217 of the applicator tip applies a tight application line of the patient sample on the substrate. In some examples, the unbound binder 210 is preloaded into the cartridge 216 in a preparation chamber 218 of the cartridge 216, and the patient sample 204 is added to the preparation chamber 218. The labeled unbound binder 210 conjugates with the target compound 204 in the preparation chamber 218 of the cartridge 216 in this example. The cartridge 216 can be inserted into a reader that includes the electrophoresis equipment, such as the paper onto which the prepared sample is applied, the electrodes for applying the electric potential, the optical imager, the light source, the processing circuitry to run the electrophoresis test, and the like. In other examples, the cartridge 216 itself has an integrated substrate on which the prepared patient sample 212 from the cartridge preparation chamber 218 is applied. The cartridge 216 can have an integrated patient sample collector (not shown) or have an opening into which the patient sample 204 is added to the preparation chamber 218.

Figure 3A:
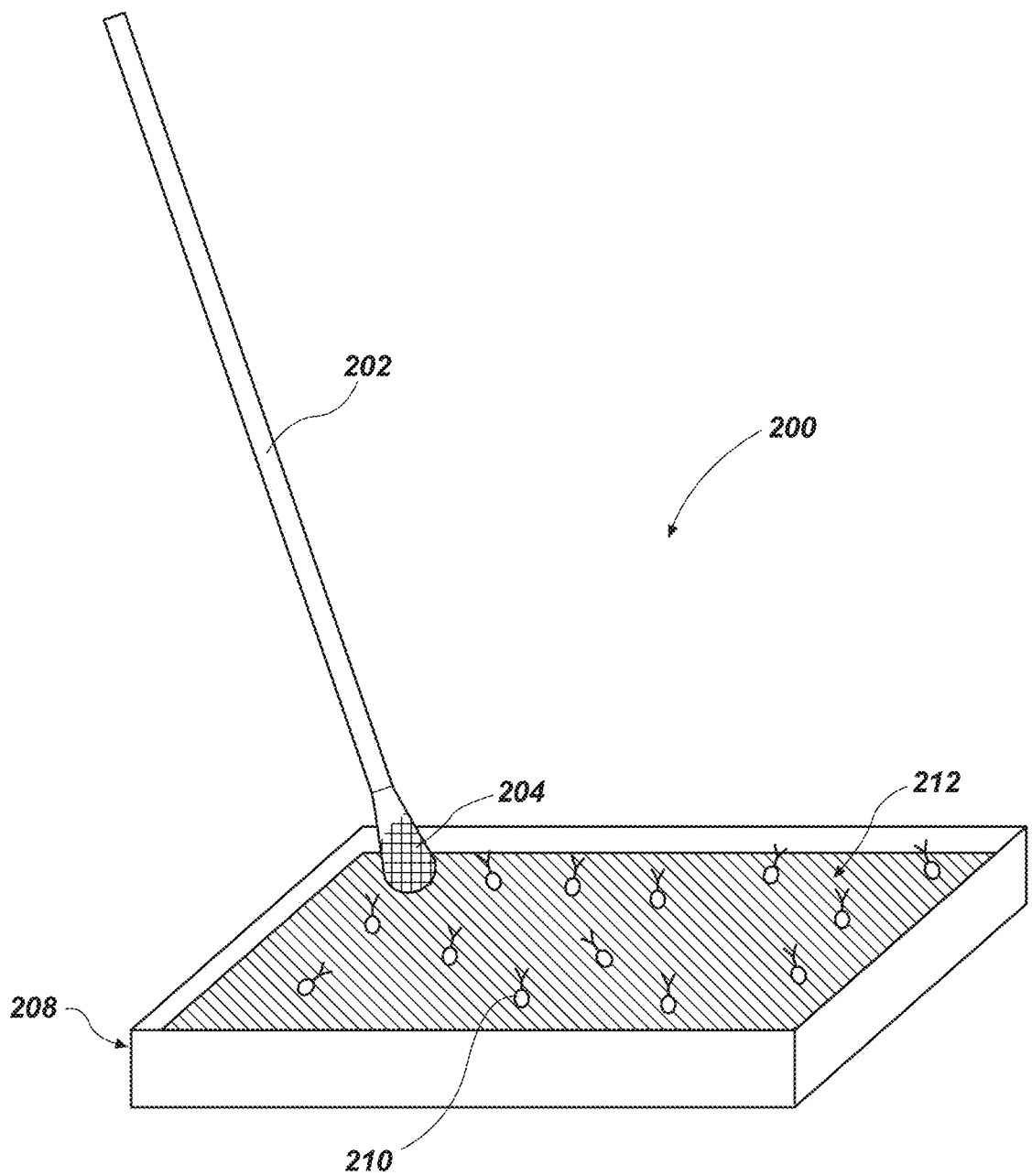
FIGS. 3A and 3B show an example patient sample and patient sample preparation without a target compound or biomarker.
Figure 3B:
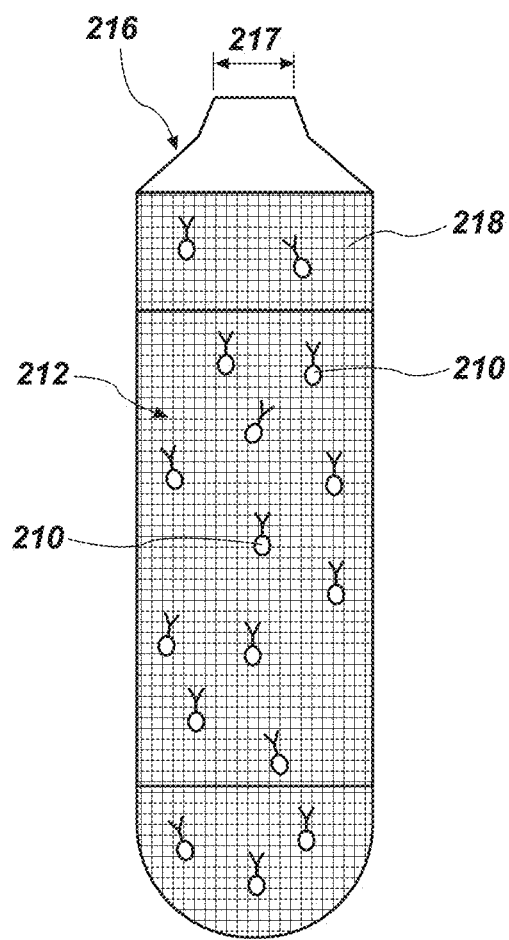

FIGS. 3A and 3B show a patient sample preparation 200 with a patient sample collector 202 with a patient sample 204 for testing, but unlike FIGS. 2A and 2B, this patient sample 204 has no target compound—it is, for example, a healthy patient sample and produces a negative result for presence of the disease or biomarker for those diseases or pre-disease conditions in which presence of the target compound indicates disease or an be a positive sample if the disease state or pre-disease condition is detected by an absence of a target compound, such as in some hemoglobin disorders. FIG. 3A shows the patient sample collector 202 with the patient sample 204 that has no target compound, and the preparation chamber 208 that includes labeled unbound binder 210. FIG. 3B shows the prepared patient sample 212 in a cartridge 216. This prepared patient sample 212 only includes labeled unbound binder 210 suspended in the prepared patient sample fluid or tissue. The results of the applied electric potential only produce an unbound binder band imaging in this example.

Figure 4:
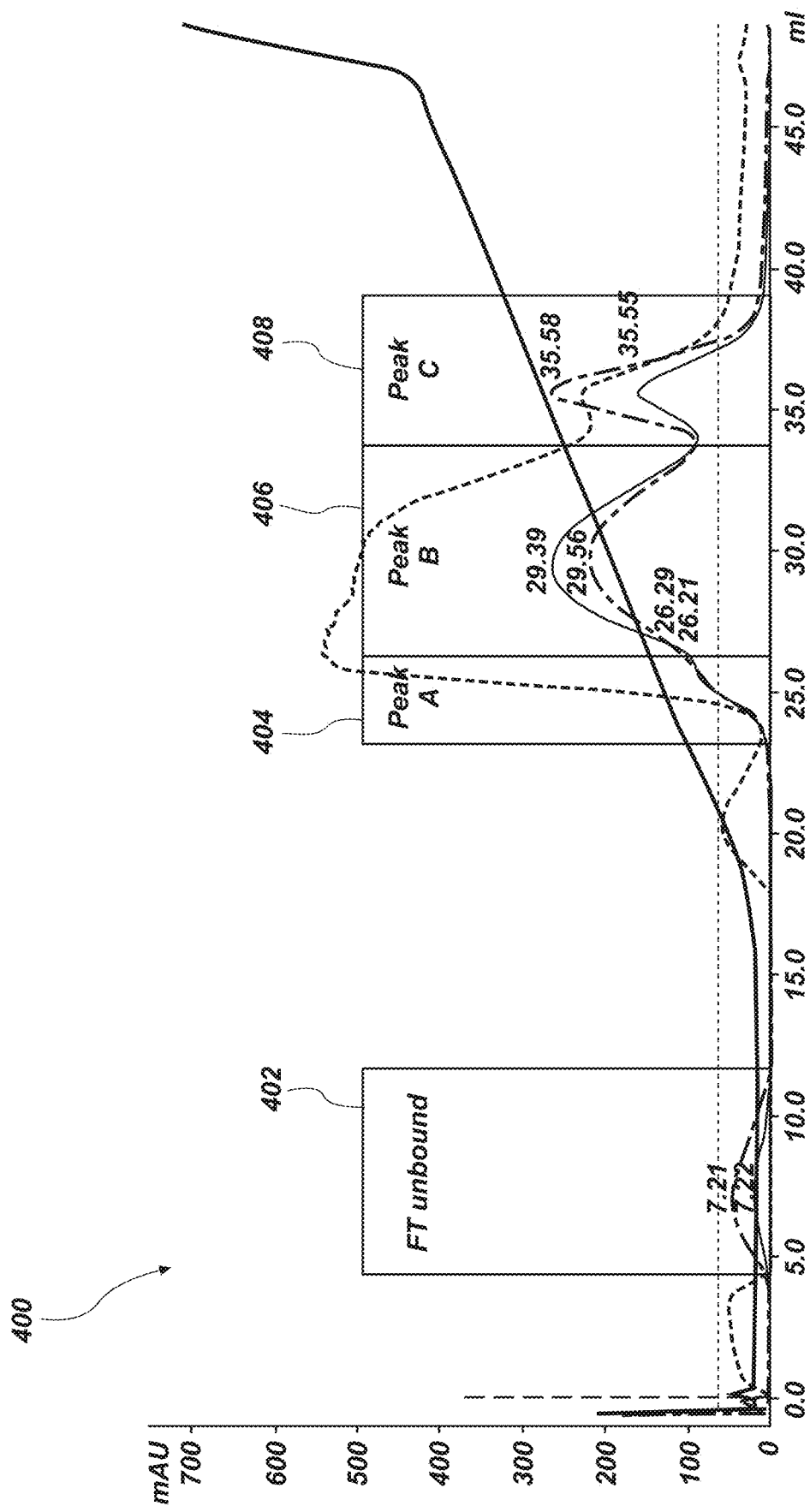
FIG. 4 shows a graph of example unbound binder and three different peak charge states of bound binder-target complex.

FIG. 4 shows a graph of anion exchange chromatography for a patient sample 400 with unbound binder 402 and fluorescently labeled binder having three distinct charge states 404, 406, 408. As discussed above, a fluor or other label with a neutral charge can be selected, in some examples, or a fluor or other label with a specific charge state is selected, as in the example labeled binder molecule shown in FIG. 4. In the example graph 400 shown in FIG. 4, a complex labeled binder is chosen that has three charge states 404, 406, and 408. Each of these charge states 404, 406, and 408 can be fractionated to the desired charge that needs to conjugate with the binder to produce the desired total net charge of the bound complex during incubation of the patient sample. Targeting a specific fluor with a known charge and then filtering the fluorescently labeled binder controls the charge and mass of the labeled binder. As shown in FIG. 4, binder molecules can have different charge states—in this example there are three charge states 404, 406, and 407—that correlate to the number of fluors bound to the binder. The three charge states 404, 406, and 408 of the labeled binder has a different charge state than unbound binder 402 alone.

The labeled binder would have a slightly heavier mass with the conjugation of the label(s) although that additional mass is negligible because the mass of a label is small comparative to the overall mass of the binder molecule. Alternatively, the fluor is selected with a specific charge state, which is discussed in more detail below in reference to FIG. 4. More complex fluors with multiple charge states need to be filtered before they are incubated with the patient sample. The filter of the fluorescently labeled binder results in a concentration of labeled binder in the same charge state and mass, which is then incubated with the patient sample. For example, fluors could have a charge of −3, −6, and −9—three distinct charge states—that are then fractionated before or after conjugating with the binder to a single charge state for the fluors or the fluorescently labeled binder, respectively. Even further, a binder can be chosen that only has a single binding site so that its charge state can only change to an expected bound charge state when the fluor conjugates to the binder—only one binding site is available to which the fluor can conjugate.

Figure 5A:
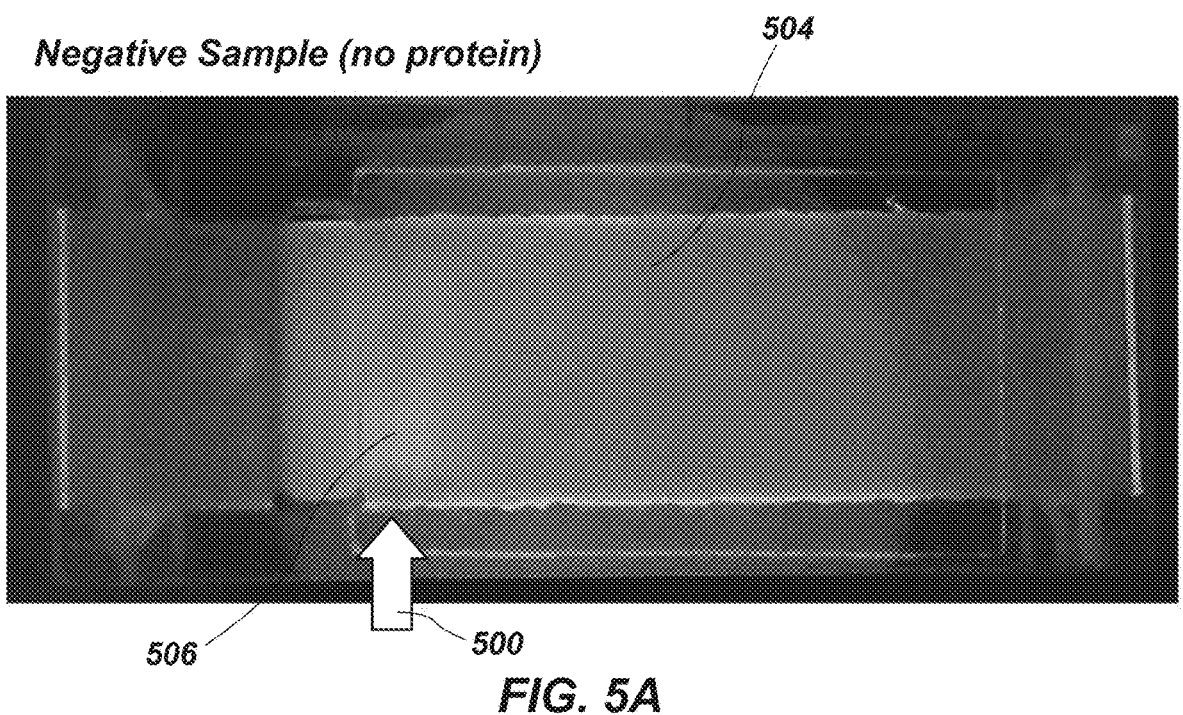
FIGS. 5A and 5B shows an example migration pattern on a substrate without a bound complex band and with a bound complex band, respectively, after an assay is complete, according to aspects of the disclosure.
Figure 5B:
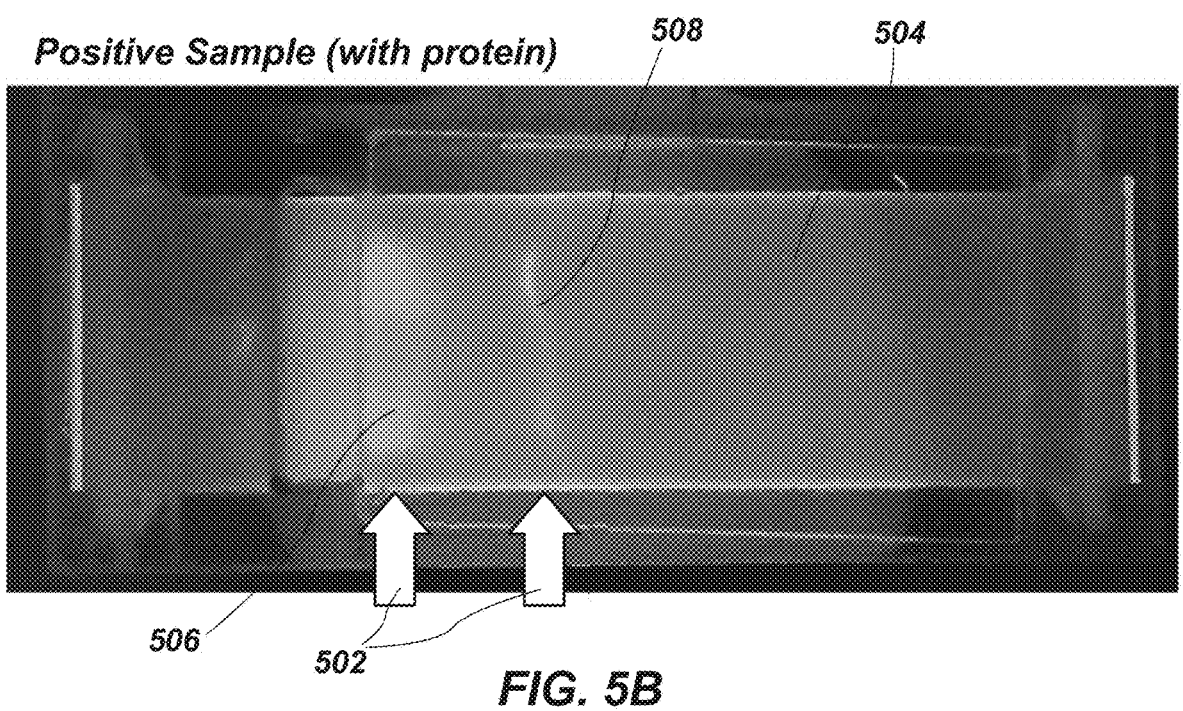

FIGS. 5A and 5B show migration patterns 500, 502 on a substrate 504 for a negative sample—having no presence of the target compound—and a positive sample—having presence of the target compound—respectively. FIG. 5A shows a sample applied to an electrophoresis paper with an unbound binder band 506 that appears near the site on the substrate 504 where the prepared patient sample is applied. No marker compound is included in this example. The patient sample has no target compound. The only band that appears is the unbound binder band 506. Because its migration pattern is known and no bound complex band appeared, this patient sample can be deemed to have had a successful run (the unbound binder band appeared with an expected migration pattern) and is negative for the target compound (no bound complex band appeared in the successful run). FIG. 5B shows the same unbound binder band 506 in approximately the same location on the substrate 504—in its expected migration pattern based on its known and fixed mass and charge state. FIG. 5B also includes a target compound band 508 that has a migration pattern that differs from the unbound binder band 506. The target compound band 508 migrated further and is thinner or is a "tighter" band than the unbound binder band 506, for example. The comparison of these and other characteristics of the migration pattern of the bound complex band 508 to the migration pattern of the unbound binder 506 indicates presence of the target compound in the patient sample, which is a positive or infected sample. Additionally, the intensity of the target compound band 508 could be analyzed to determine quantification values, such as its concentration, which is discussed in more detail below.

Figure 6A:
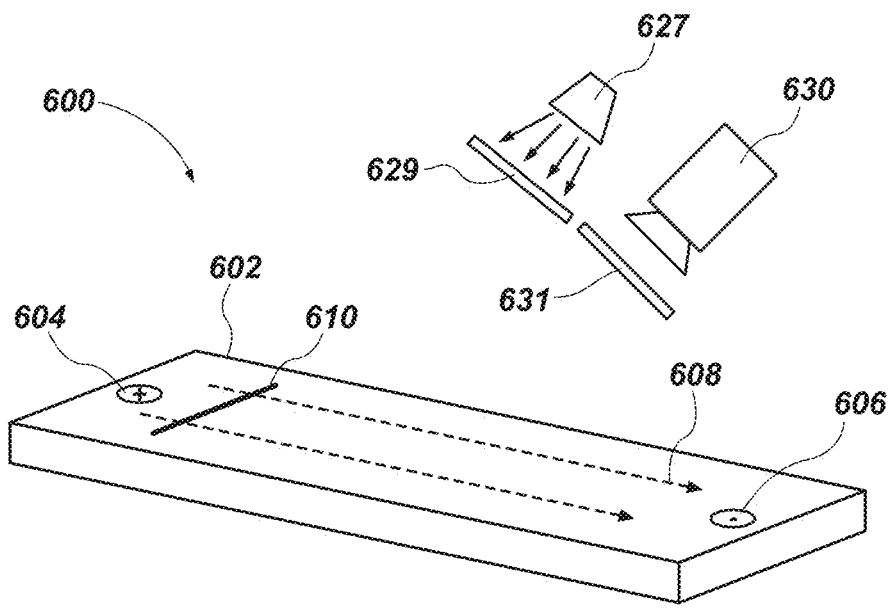
FIGS. 6A and 6B show an example diagnostic system with an optical imager and substrates with bound complex before and during or after the assay, respectively, is complete.
Figure 6B:
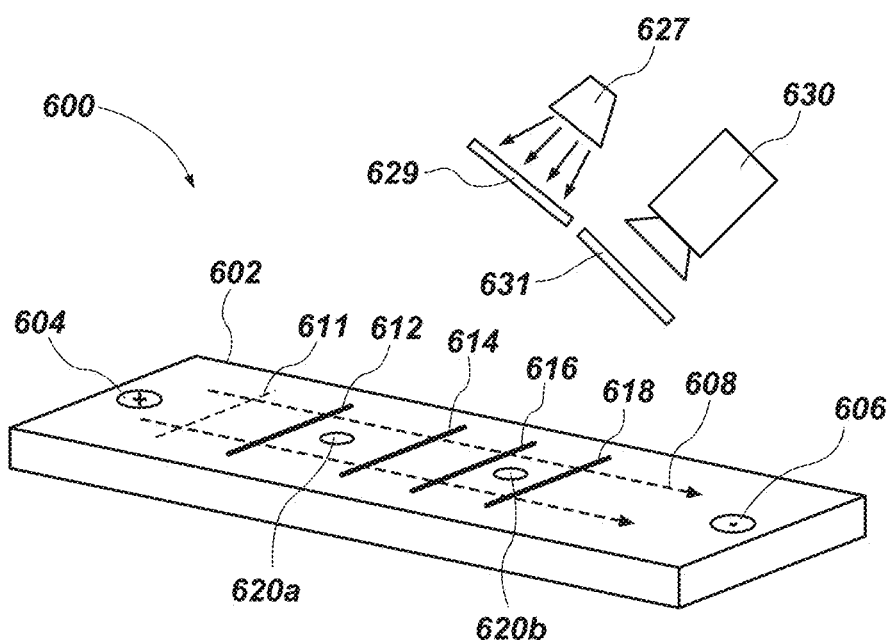

FIGS. 6A-6B illustrate an example electrophoresis system 600 that includes an electrophoresis substrate 602, electrodes 604, 606, patient sample 610 and an optical imager 630. Results of the electrophoresis analysis are optically captured by the optical imager. A light source 627 can be used to assist the capture of the results, with the light source 627 emitting light that is then reflected or transmitted through the electrophoresis paper 602 to help with imaging or visualizing the electrophoresis results on the paper. The wavelength characteristics of the light can be controlled by excitation filter 629 and the wavelengths observed by optical imager by emission filter 631. These filters are particularly important when using fluorescent labels to separate excitation light from fluorescent emissions.

FIG. 6A illustrates the initial set-up of the electrophoresis process. The electrophoresis paper 602 can have a buffer solution deposited on it to assist with establishing the electrical conductivity between the two electrodes 604 and 606. A prepared patient sample 610 is placed on the electrophoresis paper 602 in a controlled manner in this example. In the example shown in FIG. 6A, the patient sample 610 is shown deposited on the paper 602 as a line. The precision or control with which the prepared patient sample is deposited onto the electrophoresis paper 602 correlates with "tighter" bands in the migration pattern. If the sample begins from a relatively narrow starting location, its migration in a migration direction 608 is more uniform than if it begins migrating from a smeared or spread out location. Tighter bands help in band comparison and analysis because the images are compared by pixels, band intensity, location, and width, which are all improved with the control over the migration of the compounds after controlled application of the prepared patient sample on the substrate. Additionally, the patient sample 610 can include added compounds, such as one or more marker compounds, as discussed above.

For example, the one or more markers can have known migration rates or distances for a given applied voltage or voltage application time. Alternatively, these marker compounds can normalize the results of the electrophoresis process by having migration rates relative to the sample. Relying on relative migration rates, rather than absolute values, reduces the calibration needed between tests. Sample-to-sample variability makes absolute value determinations difficult because prepared samples, environmental conditions, and other test characteristics may vary or not be precisely the same between tests. The relative comparison serves to normalize this test-to-test calibration issue.

FIG. 6B illustrates the completed electrophoresis run of the patient sample shown in FIG. 6A. After applying an electric potential, via electrodes 604 and 606, for a time period, the patient sample 610 has separated into the various bands, 612, 614, 616 and 618, which have moved in a migration direction 608 from an initial patient sample location 611. Additionally, added markers 620a and 620b have separated from the initial patient sample 610 and have moved along the length of the electrophoresis substrate 602. The intensity, location, thickness or other band characteristics or of the migration pattern of the various bands 612, 614, 616 and 618 can be used to identify the components, and their relative proportions, of the initial patient sample 610. The optical image 630 captures image(s) of this migration pattern on the electrophoresis paper 602 during or after the electrophoresis run. Those captured image(s) are processed to identify the compounds represented by the various bands 612, 614, 616 and 618 and their relative proportions.

Figure 7:
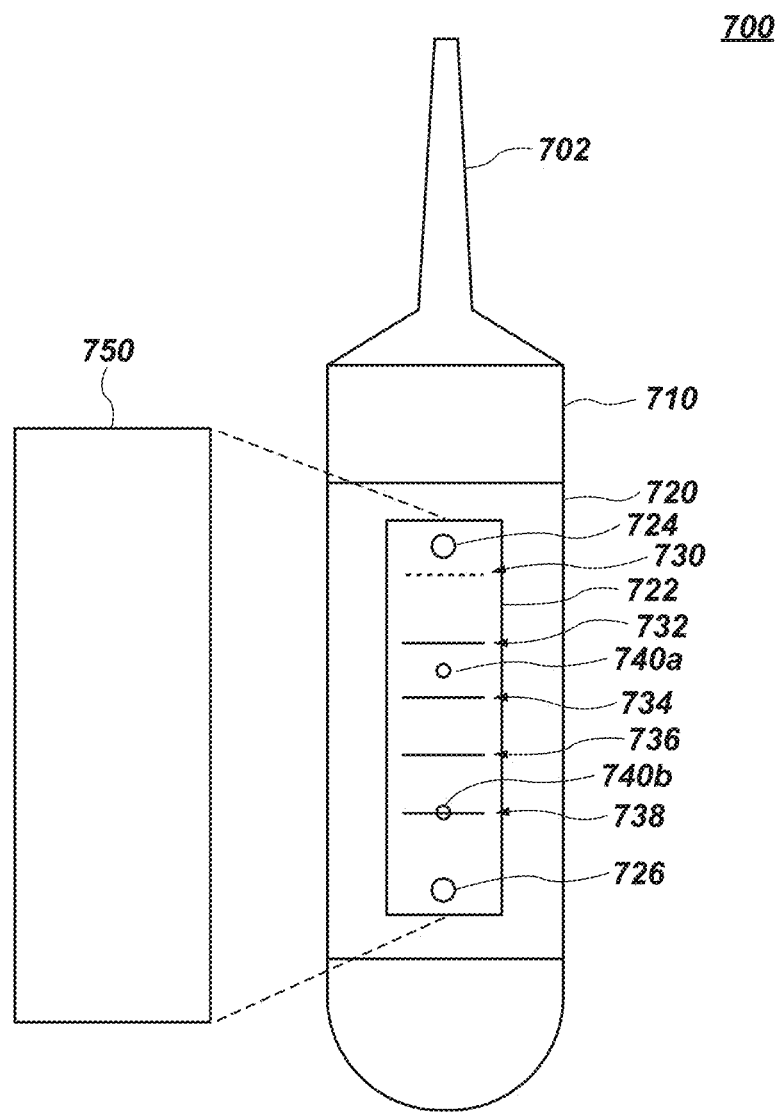
FIG. 7 shows an example patient sample cartridge with an integrated substrate that shows a migration pattern of a bound complex.

FIG. 7 illustrates an example cartridge 700 having an integrated sample collector 702, cartridge body 710, and various patient sample analysis systems in relation to the cartridge 700. Other example cartridges have variations of sample collectors or have no sample collector. The patient sample analysis systems can be included on a reader into which the cartridge 700 is inserted or received, the cartridge 700 can be inserted or received in a specific alignment or orientation in relation to the patient analysis systems of the reader. Additionally, one or more portions of or a complete patient sample analysis system can be included with the cartridge 700.

As shown in FIG. 7, the patient sample is deposited on the substrate 722 at a starting location 730. When a potential is applied across the two electrodes 724, 726, the patient sample begins to migrate across the substrate 722 to ultimately separate into four distinct bands 732, 734, 736 and 738 in its migration pattern, which is shown through a window 750 of the cartridge. Each band corresponds to a compound in the prepared patient sample. As discussed throughout this disclosure, the compounds can be identified based on their migration across the electrophoresis paper 722. Additionally, markers 740*a* and 740*b* were included in the prepared patient sample to assist with the band analysis, as discussed above. In the example shown, marker 740*a* is positioned between bands 732 and 734. The positioning of marker 740*a* between the two bands 732, 734 can helps differentiate each of the bands 732, 734 during analysis of the band data to give a relative point of reference—marker 740*a*—to clearly differentiate between band 732 and 734.

The other marker 740*b* in FIG. 7 is shown positioned with band 738. Marker 740*b* was selected to have a different total net charge and mass as the target compound associated with band 738. Band 738 migrates to the same location as marker band 740*b*, which indicates presence of the target compound because the total net charge and total net mass of the marker is known. The marker needs different optical characteristics to separate it from the co-migrating band. Any compound with a migration pattern that matches it, includes the target compound. The marker total net charge and total net mass are selected to intentionally match that of the bound target compound if it exists in the patient sample. For example, it could emit a different wavelength than the bound complex to allow both molecules to co-migrate but remain individually detectable.

Imaging of the electrophoresis substrate 722 and the bands and markers thereon can be performed using a set or varying spectrum of light or optical imaging devices and techniques, to capture a variety of information for use in analysis of the bands. In various lighting conditions and spectrums, different aspects of the bands can be more easily ascertained, such as band position and intensity. Additionally, the markers can be selected to fluoresce in response to excitation lighting, which makes it easier to determine a position of a marker relative to a band on the electrophoresis substrate 722. Multiple different fluorescing labels could be used so they can be optically distinguished. Alternatively, imaging of the electrophoresis paper 722 and the migration pattern can be performed using any suitable optical imaging device, such as a digital camera. The cartridge 700 can be imaged using the digital camera, such as by a cell phone camera, and the captured image can be transferred to a device or system for analysis or evaluation. Such functionality can also be a secondary analysis, or verification, method to support the optical imager of a reader into which the cartridge is fitted for the assay.

Because the bound complex is labeled, in this example with a fluorescent label or "fluor", the system in FIGS. 7A and 7B show a light source 627 with a filter 629. The light source 627 is the excitation energy source that emits light towards the sample to excite the fluors attached to the bound complex. In the example shown in FIGS. 7A and 7B, the light source 627 is a white light source with a filter 629 that permits only an excitation wavelength of light from the white light to be transmitted towards the substrate to excite the fluors conjugated to the bound complex. The filter of the light source can vary the wavelength, as needed, which allows it to transmit a range of wavelengths at the substrate that can excite a variety of fluors. In these examples, the optical imager 630 may also have a filter 631 that only permits light of the wavelength emitted by the excited fluors after excitation to the optical imager. In other examples (not shown), the light source 627 emits light of an excitation wavelength for the fluors and does not need a filter. In this alternative example, the optical imager can still include a filter to target the wavelength of light emitted by the excited fluors.

Figure 8:
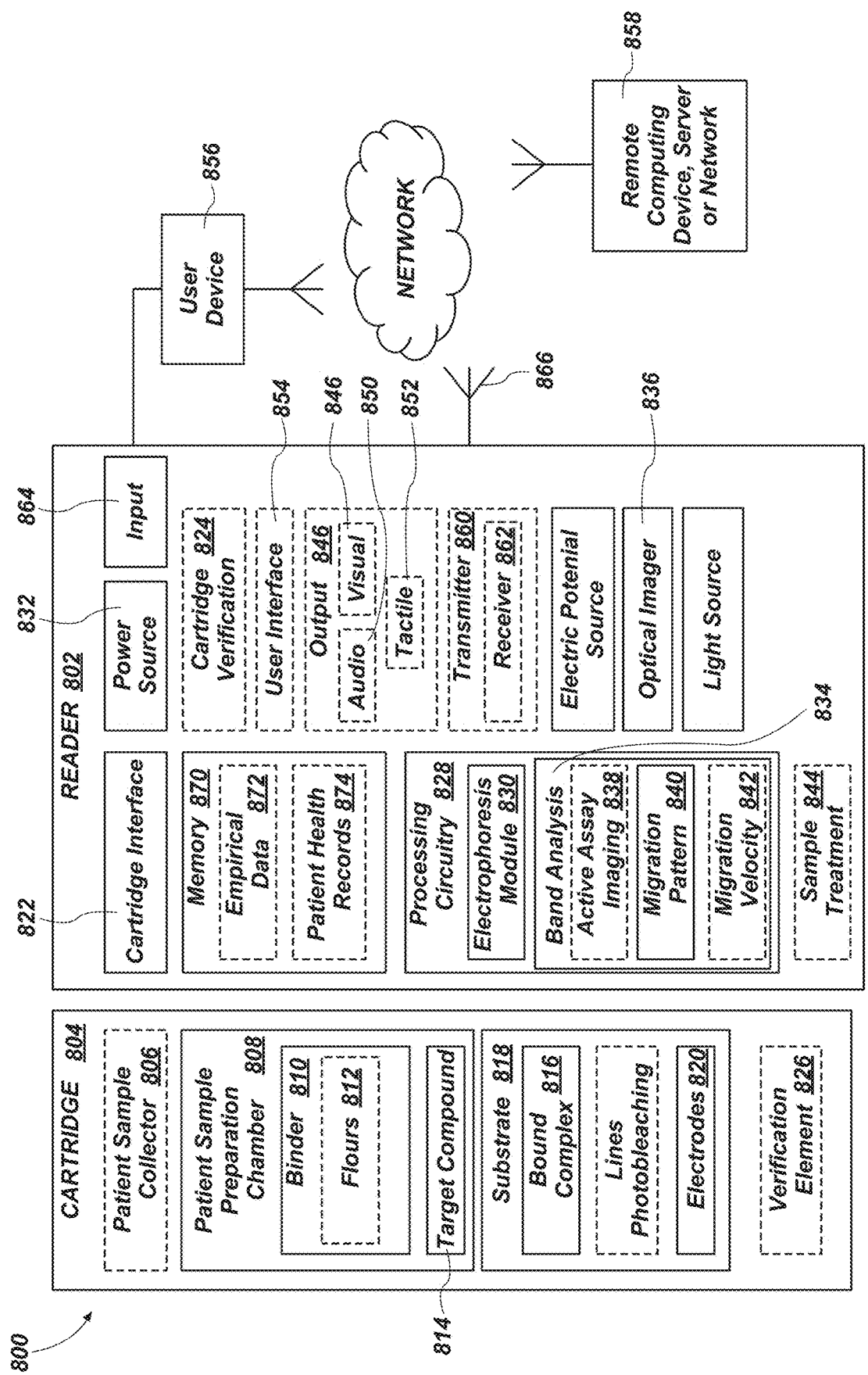
FIG. 8 is an example diagnostics system, according to aspects of the disclosure.

FIG. 8 illustrates an example system 800 with a reader 802 and a patient sample cartridge 804. The reader 802 can include all or a portion of the required systems or elements required to perform analysis of a patient sample. The cartridge 804 includes a patient sample collector 806 that could either directly collect the patient's sample or could receive a collected patient sample to facilitate the patient sample being added to the patient sample preparation chamber. In the example shown in FIG. 8, binder 810 with conjugated fluors 812 is included in the patient sample preparation chamber 808. It is mixed with target compound 814 so it conjugates with the patient sample to create a bound complex with fluors 816, as discussed above. The fluorescent bound complex 816 is applied to the substrate 818, which is also included in the cartridge 804 in this example. This example cartridge 804 also has electrodes 820 coupled to or placed on the substrate 818 for applying the electric potential after the cartridge 804 is inserted into a cartridge interface 822 of the reader 802.

The reader 802 includes a housing that surrounds and encloses some portion or all of the reader components. Any one or more components of the reader can be external to the reader housing, as needed or desired. As previously discussed, the housing of the reader 802 is constructed of suitable materials which may involve a suitably robust construction such that the reader is rugged and portable. Alternatively, the reader 802 can be designed for use in a permanent or semi-permanent location, such as in a clinic or laboratory. Example materials that can be included in the housing include plastics, metals, and composites.

The housing can be constructed of multiple or a singular material and can include geometry or structural features that enhance the usability of the reader 802. Such features can include a smooth outer surface that is easily cleaned, grips or handles for carrying the reader 802, shock protection or increased structural strength in locations to prevent damage to the internal components of the reader 802, insulation or heat dissipation structure(s) assist with maintaining a desired or a stable temperature, or range, within the housing, a membrane or construction to prevent the intrusion of moisture or dust into the interior of the reader 802, connections, ports or interfaces for connecting the reader 802 to an external element or device using a physical or wireless connection, instructions regarding the use of the reader 802, identification markings such as a serial number or additional necessary or desirable features that can facilitate the safe, effective, efficient or proper use of the reader 802. The housing can feature access points, such as removable or openable panels, to allow access to the interior of the reader 802 for maintenance or repair of the internal components, elements or systems of the reader 802. Additionally, the housing of the reader 802 can be removable or separable from the other components, elements, or systems of the reader 802, allowing the replacement of the housing, easing the cleaning of the housing, providing access to the components, elements or systems of the reader 802 or other abilities that require or are made easier by the removal of the housing of the reader 802.

The housing of the reader 802 includes a cartridge interface 822 that interacts with or engages the patient sample cartridge 804 for analysis of a patient sample, such as the patient sample cartridge 804 shown in FIG. 7. The cartridge interface 822 can be a slot that is shaped to receive the cartridge 804. The user inserts the cartridge 804 into the slot in preparation for analysis of the patient sample. The slot can include internal geometry that aligns or orients the inserted cartridge 804 in a proper alignment or orientation for the components, elements or systems of the reader 802 to perform the requisite or desired analysis of the patient sample contained within the cartridge 804. For example, the cartridge interface 822 can accept a variety of cartridges having different cross-sections, such as square, rectangular, and circular cross-sections. The unique shape of each cartridge—the unique cross-section—can interact with the geometry of the cartridge interface 822 to properly align the cartridge 804 within the reader 802 for analysis.

The reader 802 can also include a cartridge verification system 824. The cartridge verification system 824 can be integrated with or separate from the cartridge interface 822 or can be included internal to or external from the reader 802. The cartridge verification system 824, in this example shown in FIG. 8, is integrated within the reader 802 and detects a verification element 826 associated with the cartridge 804 when it engages with the cartridge interface 822, such as a QR code, bar code, or other unique identifier. The cartridge verification system 824 can verify the legitimacy of a cartridge 804 to assist with efficient and effective analysis of a patient sample. Additionally, verification of the cartridge 804 can include determining that the cartridge 804 has not been previously used. The reuse of cartridges can be allowed or not, based on testing or manufacturer requirements, and the verification system 824 can be used to enforce the desired or required limitation on reuse of a cartridge 804. Once the cartridge 804 is verified, further analysis of a patient sample contained within the cartridge 804 can be allowed to proceed. The verification of the cartridge 804 can be the threshold analysis of the in vitro diagnostics process of the patient sample, in some examples. This verification can include limiting the analysis to a test within multiple test options of the patient sample that are available in the reader 802 based on the cartridge verification.

A positive engagement or lock in the reader 802 can engage the cartridge 804 when properly and fully inserted. This engagement can also provide a tactile, audible, or visual cue to the user to signify proper insertion or interfacing of the cartridge 804 and reader 802. An example positive engagement or lock can include a notch and protrusion arrangement, the notch is sized to receive and releasably restrain the protrusion when engaged such that the notch of one element, the reader 802 or cartridge 804, engages the protrusion on the opposite element, reader 802 or cartridge 804, to releasably connect, interface with or engage the two elements, the reader 802 and cartridge 804, together. When prompted, such as when the analysis is completed or in a cartridge error situation, the user can be alerted to remove the cartridge 804 from the reader 802.

Also, the reader 802 includes processing circuitry 828 that has multiple modules that prepare the patient sample, runt the test on the sample, and analyze the results. The processing circuitry 828 has an electrophoresis module 830 that can run the test, analyze the results, and optionally prepare the sample for the test. The processing circuitry can alter the processing of the sample analysis data based on the type of cartridge 804 inserted within the reader 802.

Insertion of the cartridge 804 into the cartridge interface 822 of the reader 802 can automatically initiate or prompt a user to initiate analysis of the patient sample contained within the cartridge 804. An actuator or sensor can be connected to the processing circuitry 828 of the reader 802 and triggered by or sense the insertion of the cartridge 804 to automatically initiate or to prompt a user to initiate the analysis of the patient sample. Initiating analysis of the patient sample can include powering-up, preparing, or running the various analyses systems or devices, such as an electrophoresis diagnostic test, for example. In some examples, the user need only insert the cartridge 804 in the reader 802 to actuate or trigger the entire diagnostics process to an output.

The reader 802 can include a single cartridge interface 822, such as the example shown in FIG. 1, or can include multiple cartridge interfaces in the same reader. The example readers with multiple cartridge interfaces allow the reader to analyze multiple patient samples simultaneously or in succession by allowing more than one cartridge 804 to interface with the reader 802. Additionally, each of the multiple cartridge interfaces can accept the same or different cartridges to perform the same or different tests, respectively. Further, in conjunction with a multi- or single cartridge interface, a guide, rack, carousel or system can hold multiple cartridges in preparation for analysis. The guide, rack, carousel or system can feed or guide, actively or passively, cartridges to the reader by the cartridge interface allowing multiple patient samples or cartridges to be analyzed with minimal interruption between the analyses.

The electrophoresis module 830 of the processing circuitry 828 in the reader 802 shown in FIG. 8 initiates the electrophoresis test. The electrophoresis module 830, alone or in conjunction with the processing circuitry 828, can control the electrophoresis test, including electric potential application time or level. The electrophoresis module 830 can supply electrical power from a power source 832 of the reader 802 to the cartridge 804, or electrophoresis substrate directly, to establish the necessary electric potential across the electrophoresis substrate for testing.

The band analysis module 834 receives captured image(s) from an optical imager 836 and analyzes or evaluates the images or electrophoresis test results or any other band detection characteristic(s) related to or otherwise based on the electrophoresis test results. The optical imager 836 can include an imaging device, such as a digital image sensor, to capture an image of the electrophoresis substrate and the banding thereon during or at the conclusion of the electrophoresis test. Using the captured image data, each of the bands can be associated with one or more compounds or components of the patient sample and optionally the concentration of one or more components associated with a band can be determined for quantifying the target compound or biomarker concentration. The band analysis module 834 receives captured image(s) from the optical imager 836 for analysis including images captured during the active assay 838 and at the end of the active assay run when the electric potential is removed. Individually or collectively, the captured image(s) both during the active assay and at the end of the assay run create a migration pattern 840. The migration pattern 840 is based on the migration of the components in the patient same as they move across the substrate during and at the end of the assay when the electric potential is removed. While optional, the active assay imaging 838 is very helpful to show migration of the bound complex and other patient sample components as they migrate across the substrate, which helps create the migration pattern 840 for the test. The migration pattern 840 and optionally a migration velocity 842 is used by the band analysis module 834 to compare bands associated with different components of the patient sample during and after the assay run.

The reader 802 can also include an optional sample treatment chamber 844 or module that controls treatment of the patient sample within the reader 802. The sample treatment 844 can include a buffer solution for use with the electrophoresis substrate, markers to add to the patient sample, diluents or other solutions or compounds for use in the electrophoresis testing. The sample treatment(s) 844 can be contained within removable cartridges to ease replacement or change of the sample treatment 844. Alternatively, the reader 802 can include internal containers for storing the sample treatment 844. Associated tubing, systems or components can be included to facilitate the transfer of the sample treatment 844 to the cartridge 804 or other systems or components of the reader 802.

The positioning and structure of the cartridge 804 within the reader 802 can be such that it properly aligns with test components controlled by the electrophoresis module 830 when inserted into the reader 802. For example, the cartridge 804 is inserted to that the electrodes on the substrate come into electrical contact with an electric potential source and the substrate 818 is visible by the optical imager 836 for image capture during and after the test.

The reader 802 includes a light source 627, as discussed above. The light source 627 can be the same light source that excites the fluors 812 but emits light, such as white light, to help illuminate the electrophoresis substrate 818 and assist with capturing image(s) for the electrophoresis results. The light source 627 could be used for multiple reasons with the correct filter placed to target the wavelength of the desired light transmission—whether it is employed for fluorescence, image capture, or both. The light emitted by the light source 627 can have constant or varying properties, such as a wavelength and intensity or a frequency of the emitted light. The light source 627 can include one or more illumination elements to generate light having the required or desired properties to assist with imaging or analyzing the electrophoresis results.

The reader 802 can include an internal power source 832 that supplies the necessary power to run the components, elements or systems of the reader to perform analysis of patient samples or preserve a minimal, required functionality of the reader 802. The power source 832 can supply power to the processing circuitry, the electrophoresis module, the electrophoresis band detection module or other component, elements or systems of the reader. The power source 832 can include one or more batteries or other energy storage devices that provide a required or desired level of power for the reader 802. Additionally, the power source 832 or a portion thereof can be external to the reader 802 and connected thereto as needed or required. External power sources can include batteries or other energy storage devices or a connection to a nearby power source such as a generator, municipal power, or solar array.

The reader 802 can include an output 846 that includes one or more audio 848, visual 850, tactile 852 or other outputs. In other examples, the output 846 is data and does not include audio, visual, or tactile outputs. The output 846 shown in FIG. 8 communicates information regarding the status of the reader 802, the results of analysis of a patient sample, instructions regarding use of the reader 802 or other information to a user or other computing device. For example, the output 846 can output data including the capture image(s) of the active assay or interpretative data that indicates presence or absence of a disorder, condition, infection, or disease in the patient sample. An example can include the identification of and quantification or partial quantification of bound complex in the patient sample.

The reader 802 can also include temperature control (not shown in FIG. 8). The temperature control can actively or passively control the temperature of at least a portion of the reader. Active temperature control can include heating or cooling a portion of the reader 802 or cartridge 804. Temperature control can also include heating one portion of the reader 802 or cartridge 804 and cooling another portion of the reader 802 or cartridge 804. The temperature control can include a refrigeration system, resistive heater, infrared heater, thermoelectric elements, radiator, or other temperature control devices or systems. Passive temperature control can include structures to contain a thermal material in portions of the reader 802 or cartridge 804. This can include containers or supporting structures for ice, hot water, ice packs, and other thermal materials, the holders retain the thermal material in portions of or about components, elements or systems of the reader 802 or cartridge 804.

The reader 802 or cartridge 804 can also include a filter. For example, the filter can remove cells from a patient sample, such as blood cells from a blood sample, which results in a patient sample of plasma or serum without blood cells. The filter can attract, extract, collect or otherwise remove unwanted components or particles in a patient sample of the cartridge 804 or concentrate the desired components or particles. Filtering the patient sample can occur as the patient sample is transferred from the cartridge 804 into the reader 802 or the patient sample can be transferred from the cartridge 804, through the filter and back into the cartridge 804 for analysis or it can be internal to the cartridge 804. The filter can include structural and chemical features that allow the filter to remove desired or required components from the patient sample. The filter can be affixed in a stationary position to contact the patient sample or can moveable through the patient sample to filter the patient sample.

Processing circuitry 828 can be included in the reader to receive input from various components, elements or systems, such as the electrophoresis module 830 of the reader 802. The processing circuitry 828 can process the received inputs to perform analysis of the patient sample and output results or data of that analysis. The processing circuitry 828 can initiate or control the analysis of a patient sample within a cartridge 804. The processing circuitry 828 can include preset routines, which may be defaults or selectable by the user, that can be executed by the reader to analyze a patient sample. The preset routines can include prompts for user input received from a user interface 854 or input from another computing device or the processing circuitry can prompt a user for input before, during, or after analysis of a patient sample. User prompts can include acknowledgement or authorization to proceed through one or more portions of the analysis process. Alternatively, the processing circuitry 828 can initiate, perform, or direct the analysis of the patient sample automatically without user prompts. The processing circuitry 828 can proceed through the various processes and procedures of an analysis of a patient sample, engaging any one or more of the reader 802, remote or near transmission system or computing devices, and collecting the analysis data. The processing circuitry 828 can further automatically process the collected data and transmit a result to a user or other, including an indication the analysis is complete, information regarding the analysis or other indications. The processing circuitry 828 can also transmit the collected data to an external system or device for processing and can transmit a result to the user or the result can be transmitted by one or more of an external system, computing device, or server, such as a user device 856 or a remote computing device, server, or network 858.

The reader 802 can communicate with other remote computing device(s), server(s), or network(s) 858 through data transmitted and received from a transmitter 860 or receiver 860, respectively, which in this example are integrated in a transceiver. The data transmission can occur through a physical connection or input 864, such as a local area network (LAN), Universal Serial Bus (USB), or a wireless connection 866, such as Bluetooth®, for example. In an example, the reader 802 can communicate with a remote computing device, server, or network 858 over a network 868, which allows the reader 802 to upload patient sample analysis to a patient's health records stored on the remote server, for example. The reader 802 can transmit or receive communication to and from the reader 802 and another device or system 856, 858. In another example, information on the patient can be downloaded to the reader 802 and output to a display integrated in the user interface 854, for example, or output or used in the analysis(es). Additionally, a local user device 856 can be connected to the reader 802 for user control or interaction with the reader 802 during or after the assay is run. For example, a user tablet or laptop 856 can be connected to the reader 802 by short range communication, which allows the user tablet 856 to receive test data and control the data analysis and results.

The reader 802 can include an internal memory 870 that has various data stores including an optional empirical data store 872 and a patient health records data store 874, by way of example as shown in FIG. 8. Other data can be stored in the reader's memory 870, as needed. The empirical data store 872 can receive data about other assays including band analysis data that helps identify and quantify detected bound complex 816, for example. Empirical data known or previously captured as being associated with a known component can be used as a guide to evaluate whether a band is associated with a that component in the patient sample. It can also serve as a way to store data on the tests being run, determine trends, and export the data to remote computers, servers, or networks 858 for further analysis. The memory 870 can also include a patient health record data store 874 that includes information about a particular patient that is stored internally or transmitted to a remote computer, server, or network 858.

Figure 9A:
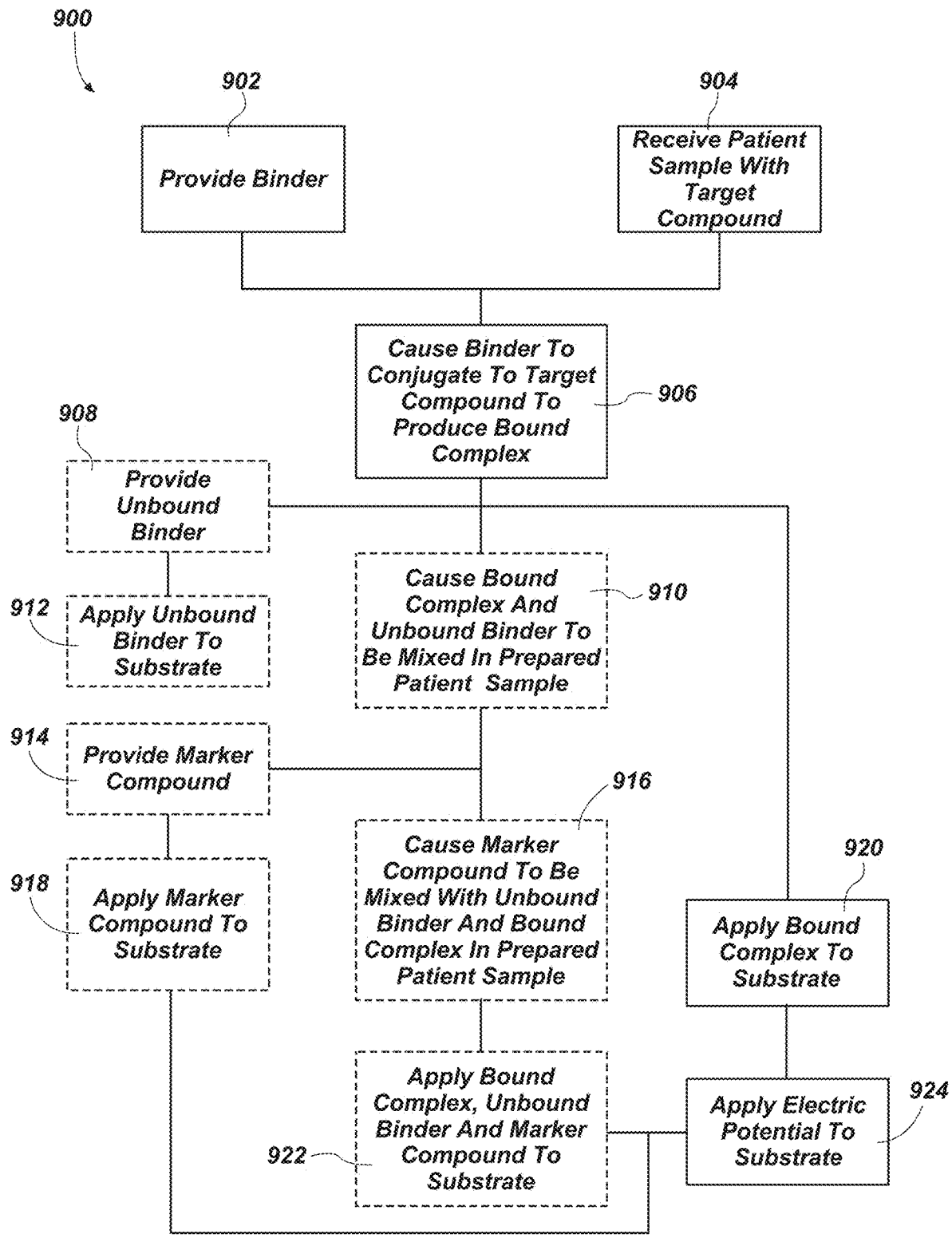
FIGS. 9A and 9B are process flow diagrams to identify presence of a compound in a patient sample, according to aspects of the disclosure.
Figure 9B:
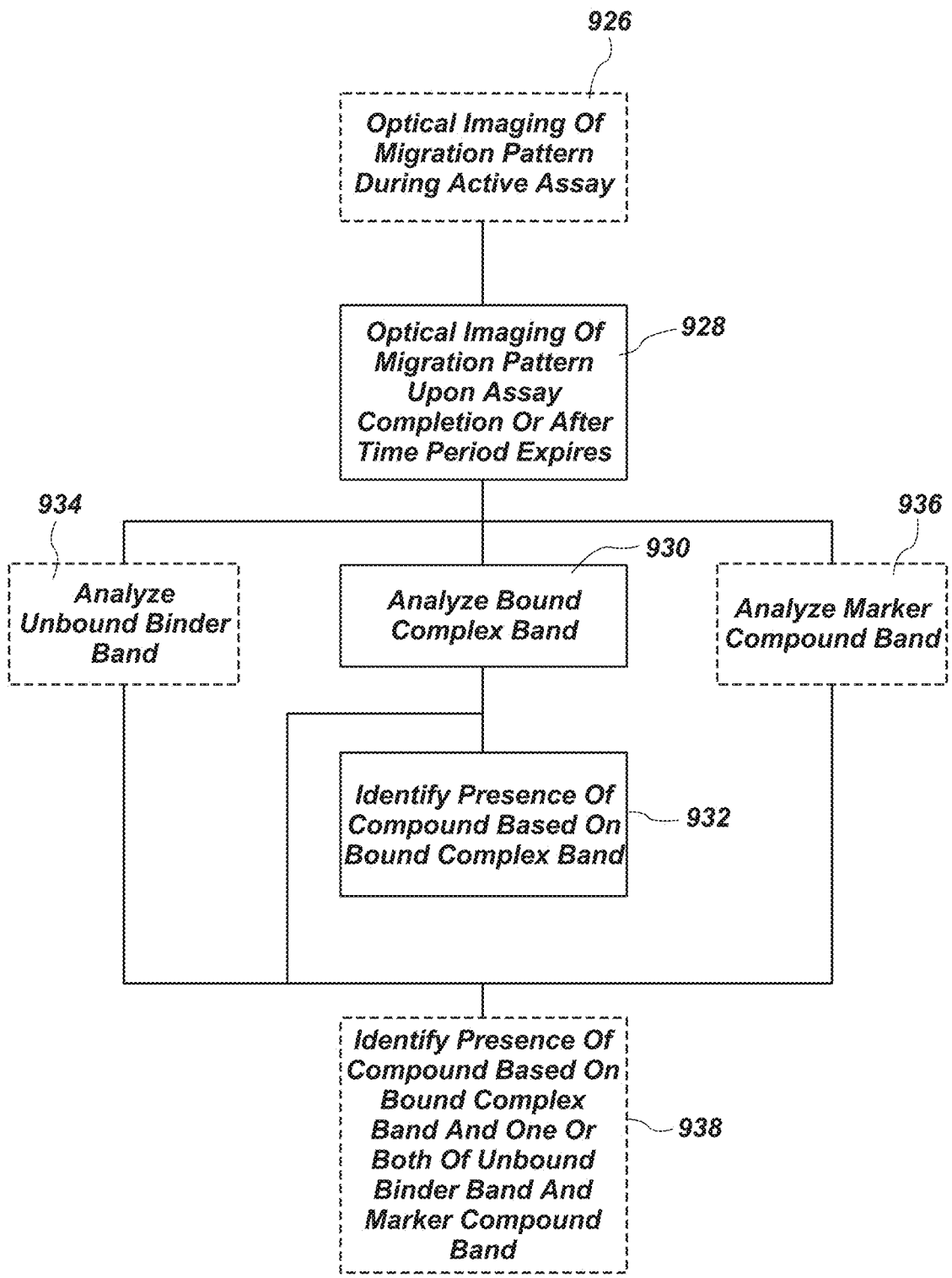

FIGS. 9A and 9B show steps in a method of identifying presence of a target compound or biomarker in a patient sample 900. The binder is provided 902 and a patient sample with a compound is received 904. The binder is caused to conjugate with the target compound to produce a bound complex 906, which can be accomplished by incubating the binder and target compound for a period of time, for example. In some example, unbound binder is provided 908 and the bound complex and unbound binder that does not conjugate with target compound is mixed in the prepared patient sample 910. Alternatively, the unbound binder, as discussed above, can be directly applied to the substrate without mixing with the prepared patient sample 912. Further, marker compound, as discussed above, can be provided 914 and the marker compound can be caused to be mixed with the prepared patient sample 916 or the marker compound can be directly applied to the substrate 918. If no unbound binder is provided 908 and no marker compound is provided 914, then the bound complex is applied to the substrate 920. However, if the unbound binder and marker compound are both provided, then both of them along with the bound complex are applied to the substrate 922. After the substrate has the prepared patient sample, the electric potential is applied 924.

The applied electric potential 924 produces a migration pattern on the substrate. The migration pattern is optically imaged during the active assay 926 and after the assay is completed or after a predetermined period of time 928. As discussed above, the migration pattern produces bands of molecules having like charge and mass. Those bands are analyzed, and specifically in the example with a patient sample that includes the target compound, the bound complex band is analyzed 930. If no unbound binder or marker compound are present on the substrate, then the presence of the compound is determined based on the bound complex band 932. If unbound binder is present on the substrate, it produces an unbound binder band that is also analyzed 934. Likewise, if marker compound is present on the substrate, it produces a marker compound band that is analyzed 936. If unbound binder and marker compound are present, then presence of the target compound is identified based on the bound complex band and one or both of the unbound binder band and the marker compound band 938.

Figure 10A:
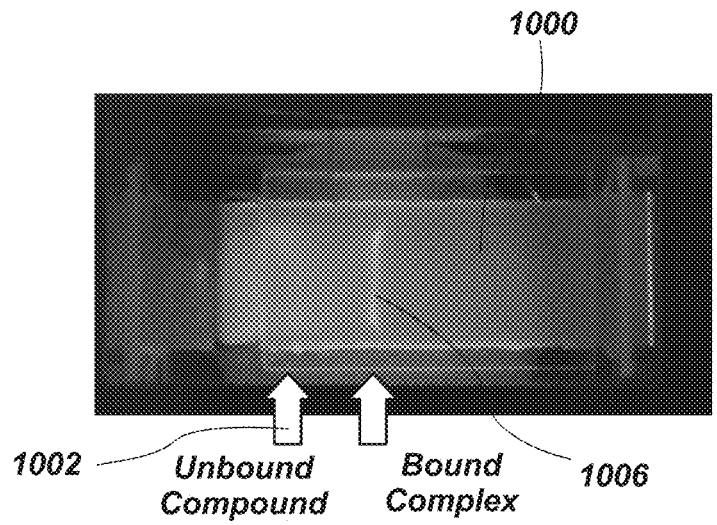
FIGS. 10A and 10B show examples of migration patterns of two patient samples having different concentrations of bound complex on a substrate, respectively.
Figure 10B:
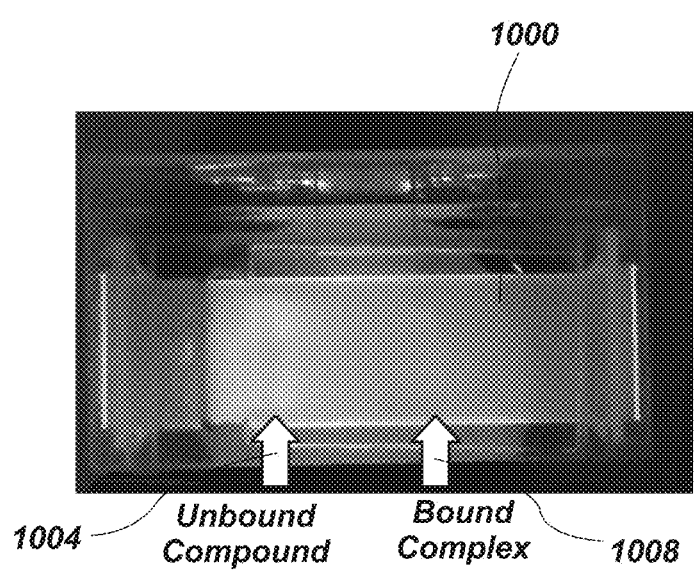

FIGS. 10A and 10B show migration patterns of substrates for two positive samples 1000—both having target compound—but each has a different concentration of the target compound. The different concentrations of the bands correlate to different intensity of the respective optically detectable bands. When these bands are optically imaged, the unbound compound band 1002 appears the same or relatively similar in the two tests with different concentrations of the bound complex. FIG. 10A shows an unbound compound band 1002 with relatively similar band characteristics like migration velocity, pixel intensity, and width to the unbound compound band 1004 in FIG. 10B. The unbound compound bands 1002 and 1004 have similar band characteristics because their controlled charge and mass produces a similar migration pattern. The bound complex band 1006 in FIG. 10A have a higher concentration than the bound complex band 1008 in FIG. 10B. These bands 1006, 1008 differ substantially in pixel intensity and width.

Figure 11:
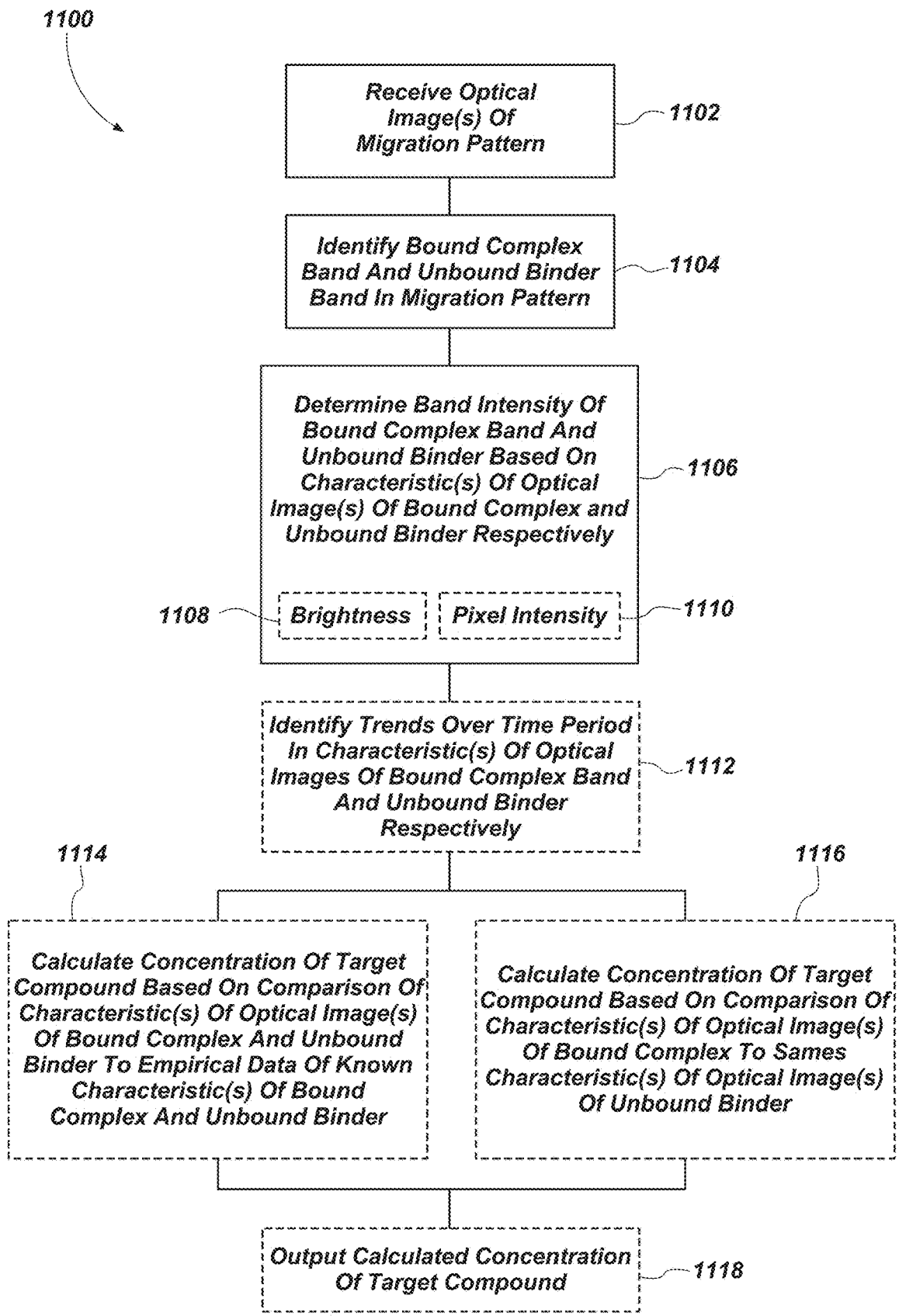
FIG. 11 shows an example process flow diagram of analyzing band intensity of unbound binder and bound complex in a migration pattern to determine a concentration of the compound.

FIG. 11 shows an example method of analyzing band intensity of unbound binder and bound complex in a patient sample 1100. This band intensity analysis can determine quantitative results on the concentration of the target compound in the patient sample. The processor can receive optical images of a migration pattern 1102. The migration pattern includes multiple bands. As discussed above, a bound complex band can be identified and, in this example shown in FIG. 11, an unbound binder band is also identified 1104. An intensity of the bound complex band and the unbound binder are determined based on characteristics of the received optical images for the bound complex and the unbound binder, respectively, 1106. The characteristics can include brightness 1108 of each band and the pixel intensity 1110 of each band. In some examples, trends in these characteristics are identified over a period of time 1112. The concentration of the target compound is based on analysis of the characteristics of the band intensity for each band.

In one example, the concentration of the target compound is calculated based on a comparison of the characteristics of the optical images—such as brightness or pixel intensity—to empirical data known to have discrete levels of target compound concentration in the bound complex band and unbound binder in the unbound binder band 1114. In other examples, the concentration of the target compound is calculated based on a relative comparison of the characteristics of the optical images—the brightness or pixel intensity—between the bands 1116. This means that the sensed brightness or pixel intensity of the bound complex is compared to the brightness or pixel intensity of the unbound binder having a known concentration of target compound. The unbound binder differential or relative comparison correlates to the concentration of the target compound in the bound complex. The calculated concentration of the target compound in then output 1118 on an output, such as a user interface of the reader, or transmitted to a user device or remote computer, server, or network, in some examples.

Though certain elements, aspects, components or the like are described in relation to one embodiment or example, such as an example diagnostic system or method, those elements, aspects, components or the like can be including with any other diagnostic system or method, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents.

What is claimed is:

1. A method of identifying whether a compound is present in a patient sample applied on a substrate, the substrate being electrophoresis paper or gel substrate, the method comprising:
    providing a binder having a binder charge profile;
    receiving the patient sample with the compound;
    labeling either the binder or the compound to produce a labeled binder or a labeled compound, respectively;
    causing the labeled binder to bind to the compound or the binder to bind to the labeled compound, depending on whether the binder or the compound is labeled, to produce a labeled bound complex having a compound charge state, the compound charge state based on the binder charge profile;
    applying the labeled bound complex to the substrate;
    applying an electric potential to the substrate;
    in response to the applied electric potential, generating a migration pattern of the labeled bound complex based in the compound charge state, the migration pattern generated as the bound complex migrates across the substrate at a migration velocity over a time period to produce a labeled bound complex band on the substrate; and
    identifying presence of the compound based the labeled bound complex band and one or both of the migration pattern and the migration velocity.

2. The method of claim 1, wherein the binder includes an antibody, an antigen, a lampribody, or a synthetic binder.

3. The method of claim 1, wherein the binder charge profile correlates with a total net charge of the compound.

4. The method of claim 1, wherein the compound is a virus or a portion of a virus.

5. The method of claim 1, further comprising:
    separating the labeled bound complex into multiple compound charge states;
    generating a migration pattern of the labeled bound complex that includes producing a respective labeled bound complex band for each of the multiple compound charge states of the labeled bound complex; and
    identifying presence of the compound based on the multiple respective labeled bound complex bands and one or both of the migration pattern and the migration velocity.

6. The method of claim 1, further comprising labeling the binder to produce a labeled binder, and causing the labeled binder to bind to the compound to form the labeled bound complex.

7. The method of claim 1, wherein labeling the binder to produce the labeled binder or labeling the compound to produce the labeled compound includes causing a substance that is optically detectable to be attached to the binder or the compound, respectively.

8. The method of claim 7, wherein the substance is visible in white light.

9. The method of claim 1, wherein the labeling the binder or the compound to produce the labeled binder or the labeled compound, respectively, includes:
    adding a fluorescence label to one or both of the binder and the compound to create a labeled bound binder-target complex;
    generating the migration pattern of the labeled bound complex based on the labeled bound complex migrating across the substrate at the migration velocity over the time period, the migration pattern producing the labeled bound complex band; and
    identifying presence of the compound based on the labeled bound complex band and one or both of the migration pattern and the migration velocity.

10. The method of claim 9, wherein the fluorescence label is europium.

11. The method of claim 9, further comprising:
    transmitting energy from an excitation energy source towards the labeled bound complex band;
    detecting a fluorescence emission produced by the fluorescence label in response to the transmitted energy; and
    identifying presence of the compound based on the fluorescence emission produced by the fluorescence label, the labeled bound complex band, and one or both of the migration pattern and the migration velocity.

12. The method of claim 11, wherein transmitting the energy from the excitation energy source and detecting the fluorescence emission occur during active migration of the labeled bound complex.

13. The method of claim 11, wherein the excitation energy source is a laser.

14. The method of claim 11, wherein the excitation energy source is a light emitting diode (LED) having a wavelength or range of wavelengths with a center of 365 nanometers (nm), and the fluorescence emission has a wavelength or range of wavelengths that includes 610 nm.

15. The method of claim 1, wherein the binder has a mass, and further comprising:
    causing the labeled binder to bind to the compound or the binder to bind to the labeled compound to produce the labeled bound complex having a compound mass based on the mass of the binder; and
    generating the migration pattern of the labeled bound complex based on the compound mass and the compound charge state.

16. The method of claim 1, further comprising identifying presence of the compound based on the labeled bound complex band and the migration pattern.

17. The method of claim 1, further comprising identifying presence of the labeled compound based on the labeled bound complex band, the migration pattern, and the migration velocity of the labeled bound complex band.

18. The method of claim 1, further comprising:
    determining a band intensity of the labeled bound complex band based in part on a characteristic of an optical image of the labeled bound complex band; and
    calculating a concentration of the compound based on the band intensity of the labeled bound complex band.

19. The method of claim 18, further comprising outputting one or both of the presence of the compound in the patient sample and the concentration of the compound.

20. The method of claim 18, further comprising:
    generating the migration pattern of the labeled bound complex based on the compound charge state and a migration pattern of unbound binder based on a charge state of the unbound binder, the migration pattern of the labeled bound complex and the migration pattern of the unbound binder generated as the labeled bound complex and the unbound binder migrate across the substrate at respective migration velocities over the time period to produce the labeled bound complex band and an unbound complex band, respectively, on the substrate;
    determining a band intensity of unbound binder based on a characteristic of an optical image of the unbound binder;
    comparing the band intensity of the labeled bound complex band and the band intensity of the unbound binder band; and
    calculating a concentration of the compound based on the comparison of the band intensity of the labeled bound complex band and the band intensity of the unbound binder band.

21. The method of claim 20, further comprising capturing the optical image of the labeled bound complex band and the optical image of the unbound complex band during active migration of the labeled bound complex and the unbound binder, respectively, during the time period.

22. The method of claim 18, further comprising calculating the concentration of the compound by comparing an absolute value of the band intensity of the labeled bound complex band with an empirical band intensity absolute value or a threshold band intensity absolute value.

23. The method of claim 1, further comprising taking multiple or continuous optical images of the migration pattern of the labeled bound complex band over the time period.

24. The method of claim 1, further comprising:
    providing a marker compound having a marker concentration, the marker compound including compound with bound binder; and
    in response to the applied electric potential, generating the migration pattern of the labeled bound complex and the marker compound, the migration pattern of the marker compound generated as the marker compound migrates across the substrate at a marker migration velocity over the period of time to produce a marker compound band on the substrate.

25. The method of claim 24, further comprising identifying the presence of the compound based on comparing the labeled bound complex band to the marker compound band.

26. The method of claim 1, wherein the substrate is electrophoresis paper, and further comprising photobleaching the electrophoresis paper before applying the electric potential.

27. A diagnostic system, comprising:
    a patient sample cartridge having a patient sample with a labeled bound complex, the labeled bound complex including a labeled binder with a binder charge profile bound to a compound in the patient sample;
    a processor configured to:
        detect that the labeled bound complex is applied to a substrate;
        cause an electric potential to be applied to the substrate;
        receive a data signal that includes a migration pattern of the labeled bound complex in response to the applied electric potential, the migration pattern generated as the labeled bound complex migrates across the substrate at a migration velocity over a time period to produce a labeled bound complex band on the substrate;
    identify presence of the compound based on the labeled bound complex band and one or both of the migration pattern and the migration velocity.

* * * * *